(12) United States Patent
Rawson et al.

(10) Patent No.: US 11,607,344 B2
(45) Date of Patent: Mar. 21, 2023

(54) CUSTOMIZABLE WOUND CLOSURE DEVICE AND METHOD OF USE

(71) Applicant: Smith & Nephew PLC, Watford (GB)

(72) Inventors: Neill John Rawson, Doncaster (GB); Iain Webster, Hull (GB)

(73) Assignee: Smith & Nephew PLC, Watford (GB)

( * ) Notice: Subject to any disclaimer, the term of this patent is extended or adjusted under 35 U.S.C. 154(b) by 102 days.

(21) Appl. No.: 16/634,534

(22) PCT Filed: Jul. 23, 2018

(86) PCT No.: PCT/EP2018/069871
§ 371 (c)(1),
(2) Date: Jan. 27, 2020

(87) PCT Pub. No.: WO2019/020544
PCT Pub. Date: Jan. 31, 2019

(65) Prior Publication Data
US 2020/0179174 A1 Jun. 11, 2020

Related U.S. Application Data

(60) Provisional application No. 62/537,617, filed on Jul. 27, 2017.

(51) Int. Cl.
*A61F 13/00* (2006.01)
*A61F 13/02* (2006.01)
*A61M 1/00* (2006.01)

(52) U.S. Cl.
CPC .. *A61F 13/00068* (2013.01); *A61F 13/00029* (2013.01); *A61F 13/0216* (2013.01);
(Continued)

(58) Field of Classification Search
CPC ............ A61M 1/90; A61M 2210/1021; A61F 13/0216; A61F 13/00029; A61F 13/00068;
(Continued)

(56) References Cited

U.S. PATENT DOCUMENTS 3,194,239 A 7/1965 Sullivan et al.
3,789,851 A 2/1974 Leveen
(Continued)

FOREIGN PATENT DOCUMENTS

AU 2012261793 B2 11/2014
AU 2013206230 B2 5/2016
(Continued)

OTHER PUBLICATIONS

International Search Report and Written Opinion for Application No. PCT/EP2018/069871, dated Oct. 19, 2018, 11 pages.
(Continued)

*Primary Examiner* — Jessica Arble
(74) *Attorney, Agent, or Firm* — Knobbe, Martens, Olson & Bear, LLP

(57) ABSTRACT

A negative pressure wound closure system and methods for using such a system are described. Preferred embodiments of the invention facilitate closure of the wound by preferentially contracting to provide for movement of the tissue. Some embodiments may include wound closure devices built from smaller units that are modular, assemble-able and/or customizable.

18 Claims, 31 Drawing Sheets

(52) U.S. Cl.
CPC ............ *A61M 1/915* (2021.05); *A61M 1/916* (2021.05); *A61F 2013/00778* (2013.01); *A61M 1/966* (2021.05); *A61M 2210/1021* (2013.01)

(58) Field of Classification Search
CPC .......... A61F 2013/00778; A63H 33/06; A63H 33/08; A63H 33/082; A63H 33/084; A63H 33/086; A63H 33/088; A63F 9/12; A63F 2009/1228; A63F 2009/1232
See application file for complete search history.

(56) References Cited

U.S. PATENT DOCUMENTS

| | | | |
|---|---|---|---|
| 4,467,805 A | 8/1984 | Fukuda | |
| 4,608,041 A | 8/1986 | Nielsen et al. | |
| 4,699,134 A | 10/1987 | Samuelsen | |
| 4,815,468 A | 3/1989 | Annand | |
| 5,176,663 A | 1/1993 | Svedman et al. | |
| 5,264,218 A | 11/1993 | Rogozinski | |
| 5,376,067 A | 12/1994 | Daneshvar | |
| 5,409,472 A | 4/1995 | Rawlings et al. | |
| 5,415,715 A | 5/1995 | Delage et al. | |
| 5,423,857 A | 6/1995 | Rosenman | |
| 5,512,041 A | 4/1996 | Bogart | |
| 5,562,107 A | 10/1996 | Lavender et al. | |
| 5,584,859 A | 12/1996 | Brotz | |
| 5,636,643 A | 6/1997 | Argenta et al. | |
| 5,695,777 A | 12/1997 | Donovan et al. | |
| 6,176,868 B1 | 1/2001 | Detour | |
| 6,503,208 B1 | 1/2003 | Skovlund | |
| 6,548,727 B1 | 4/2003 | Swenson | |
| 6,566,575 B1 | 5/2003 | Stickels et al. | |
| 6,685,681 B2 | 2/2004 | Lockwood et al. | |
| 6,770,794 B2 | 8/2004 | Fleischmann | |
| 6,787,682 B2 | 9/2004 | Gilman et al. | |
| 6,977,323 B1 | 12/2005 | Swenson et al. | |
| 7,004,915 B2 | 2/2006 | Boynton et al. | |
| 7,144,390 B1 | 12/2006 | Hannigan et al. | |
| 7,315,183 B2 | 1/2008 | Hinterscher | |
| 7,351,250 B2 | 4/2008 | Zamierowski et al. | |
| 7,361,184 B2 | 4/2008 | Joshi et al. | |
| 7,438,705 B2 | 10/2008 | Karpowicz et al. | |
| 7,494,482 B2 | 2/2009 | Orgill et al. | |
| 7,615,036 B2 | 11/2009 | Joshi et al. | |
| 7,622,629 B2 | 11/2009 | Aali et al. | |
| 7,625,362 B2 | 12/2009 | Boehringer et al. | |
| 7,683,667 B2 | 3/2010 | Kim et al. | |
| 7,700,819 B2 | 4/2010 | Ambrosio et al. | |
| 7,754,937 B2 | 7/2010 | Boehringer et al. | |
| 7,779,625 B2 | 8/2010 | Joshi et al. | |
| 7,815,616 B2 | 10/2010 | Boehringer et al. | |
| 7,857,806 B2 | 12/2010 | Karpowicz et al. | |
| 7,863,495 B2 | 1/2011 | Aali | |
| 7,892,181 B2 | 2/2011 | Christensen et al. | |
| 7,896,856 B2 | 3/2011 | Petrosenko et al. | |
| 7,909,805 B2 | 3/2011 | Weston et al. | |
| 7,910,789 B2 | 3/2011 | Sinyagin | |
| 7,931,774 B2 | 4/2011 | Hall et al. | |
| 7,942,866 B2 | 5/2011 | Radl et al. | |
| 7,951,124 B2 | 5/2011 | Boehringer et al. | |
| 7,964,766 B2 | 6/2011 | Blott et al. | |
| 7,976,519 B2 | 7/2011 | Bubb et al. | |
| 7,976,524 B2 | 7/2011 | Kudo et al. | |
| 8,030,534 B2 | 10/2011 | Radl et al. | |
| 8,057,447 B2 | 11/2011 | Olson et al. | |
| 8,062,331 B2 | 11/2011 | Zamierowski et al. | |
| 8,067,662 B2 | 11/2011 | Aali et al. | |
| 8,070,773 B2 | 12/2011 | Zamierowski et al. | |
| 8,114,126 B2 | 2/2012 | Heaton et al. | |
| 8,123,781 B2 | 2/2012 | Zamierowski et al. | |
| 8,142,419 B2 | 3/2012 | Heaton et al. | |
| 8,172,816 B2 | 5/2012 | Kazala, Jr. et al. | |
| 8,187,237 B2 | 5/2012 | Seegert et al. | |
| 8,188,331 B2 | 5/2012 | Barta et al. | |
| 8,197,467 B2 | 6/2012 | Heaton et al. | |
| 8,207,392 B2 | 6/2012 | Haggstrom et al. | |
| 8,235,955 B2 | 8/2012 | Blott et al. | |
| 8,246,590 B2 | 8/2012 | Hu et al. | |
| 8,246,606 B2 | 8/2012 | Stevenson et al. | |
| 8,257,328 B2 | 9/2012 | Augustine et al. | |
| 8,273,105 B2 | 9/2012 | Cohen et al. | |
| 8,328,776 B2 | 12/2012 | Kelch et al. | |
| 8,337,411 B2 | 12/2012 | Nishtala et al. | |
| 8,353,931 B2 | 1/2013 | Stopek et al. | |
| 8,357,131 B2 | 1/2013 | Olson | |
| 8,376,972 B2 | 2/2013 | Fleischmann et al. | |
| 8,430,867 B2 | 4/2013 | Robinson et al. | |
| 8,447,375 B2 | 5/2013 | Shuler | |
| 8,454,990 B2 | 6/2013 | Canada et al. | |
| 8,460,257 B2 | 6/2013 | Locke et al. | |
| 8,481,804 B2 | 7/2013 | Timothy | |
| 8,486,032 B2 | 7/2013 | Seegert et al. | |
| 8,500,776 B2 | 8/2013 | Ebner | |
| 8,608,776 B2 | 12/2013 | Coward et al. | |
| 8,632,523 B2 | 1/2014 | Eriksson et al. | |
| 8,673,992 B2 | 3/2014 | Eckstein et al. | |
| 8,679,080 B2 | 3/2014 | Kazala, Jr. et al. | |
| 8,679,153 B2 | 3/2014 | Dennis | |
| 8,680,360 B2 | 3/2014 | Greener et al. | |
| 8,708,984 B2 | 4/2014 | Robinson et al. | |
| 8,721,629 B2 | 5/2014 | Hardman et al. | |
| 8,746,662 B2 | 6/2014 | Poppe | |
| 8,764,732 B2 | 7/2014 | Hartwell et al. | |
| 8,791,315 B2 | 7/2014 | Lattimore et al. | |
| 8,791,316 B2 | 7/2014 | Greener et al. | |
| 8,802,916 B2 | 8/2014 | Griffey et al. | |
| 8,821,535 B2 | 9/2014 | Greener | |
| 8,945,030 B2 | 2/2015 | Weston et al. | |
| 9,044,579 B2 | 6/2015 | Blott et al. | |
| 9,061,095 B2 | 6/2015 | Adie et al. | |
| 9,180,231 B2 | 11/2015 | Greener et al. | |
| 9,408,755 B2 | 8/2016 | Larsson et al. | |
| 9,421,132 B2 | 8/2016 | Dunn et al. | |
| 9,655,807 B2 | 5/2017 | Locke et al. | |
| 9,849,023 B2 | 12/2017 | Hall et al. | |
| 10,143,485 B2 | 12/2018 | Locke et al. | |
| 2001/0034499 A1 | 10/2001 | Sessions et al. | |
| 2002/0077661 A1 | 6/2002 | Saadat | |
| 2002/0161346 A1 | 10/2002 | Lockwood et al. | |
| 2004/0162512 A1 | 8/2004 | Liedtke et al. | |
| 2004/0267312 A1 | 12/2004 | Kanner et al. | |
| 2005/0142331 A1 | 6/2005 | Anderson et al. | |
| 2005/0267424 A1 | 12/2005 | Eriksson et al. | |
| 2006/0020269 A1 | 1/2006 | Cheng | |
| 2006/0058842 A1 | 3/2006 | Wilke et al. | |
| 2006/0069357 A1 | 3/2006 | Marasco | |
| 2006/0155260 A1 | 7/2006 | Blott et al. | |
| 2006/0217795 A1 | 9/2006 | Besselink et al. | |
| 2006/0271018 A1 | 11/2006 | Korf | |
| 2007/0052144 A1 | 3/2007 | Knirck et al. | |
| 2007/0104941 A1 | 5/2007 | Kameda et al. | |
| 2007/0118096 A1 | 5/2007 | Smith et al. | |
| 2007/0123973 A1 | 5/2007 | Roth et al. | |
| 2007/0129660 A1 | 6/2007 | McLeod et al. | |
| 2007/0149910 A1 | 6/2007 | Zocher | |
| 2007/0185463 A1 | 8/2007 | Mulligan | |
| 2007/0213597 A1 | 9/2007 | Wooster | |
| 2007/0282309 A1 | 12/2007 | Bengtson et al. | |
| 2008/0041401 A1 | 2/2008 | Casola et al. | |
| 2008/0108977 A1 | 5/2008 | Heaton et al. | |
| 2008/0243096 A1 | 10/2008 | Svedman | |
| 2008/0275409 A1 | 11/2008 | Kane et al. | |
| 2008/0306456 A1 | 12/2008 | Riesinger | |
| 2009/0005716 A1 | 1/2009 | Abuzaina et al. | |
| 2009/0099519 A1 | 4/2009 | Kaplan | |
| 2009/0105670 A1 | 4/2009 | Bentley et al. | |
| 2009/0117311 A1* | 5/2009 | Kuzmin ................ A63H 33/08 428/44 |
| 2009/0204423 A1 | 8/2009 | Degheest et al. | |
| 2009/0312685 A1 | 12/2009 | Olsen et al. | |
| 2010/0022990 A1 | 1/2010 | Karpowicz et al. | |
| 2010/0047324 A1 | 2/2010 | Fritz et al. | |
| 2010/0081983 A1 | 4/2010 | Zocher et al. | |
| 2010/0137775 A1 | 6/2010 | Hu et al. | |

(56) References Cited

U.S. PATENT DOCUMENTS

| | | |
|---|---|---|
| 2010/0150991 A1 | 6/2010 | Bernstein |
| 2010/0160874 A1 | 6/2010 | Robinson et al. |
| 2010/0179515 A1 | 7/2010 | Swain et al. |
| 2010/0198128 A1 | 8/2010 | Turnlund et al. |
| 2010/0262106 A1 | 10/2010 | Hartwell |
| 2010/0280468 A1 | 11/2010 | Haggstrom et al. |
| 2010/0312159 A1 | 12/2010 | Aali et al. |
| 2011/0021965 A1 | 1/2011 | Karp et al. |
| 2011/0022082 A1 | 1/2011 | Burke et al. |
| 2011/0059291 A1 | 3/2011 | Boyce et al. |
| 2011/0066096 A1 | 3/2011 | Svedman |
| 2011/0082480 A1 | 4/2011 | Viola |
| 2011/0110996 A1 | 5/2011 | Schoenberger et al. |
| 2011/0112458 A1 | 5/2011 | Holm et al. |
| 2011/0178451 A1 | 7/2011 | Robinson et al. |
| 2011/0224631 A1 | 9/2011 | Simmons et al. |
| 2011/0224632 A1 | 9/2011 | Zimnitsky et al. |
| 2011/0224634 A1 | 9/2011 | Locke et al. |
| 2011/0264138 A1 | 10/2011 | Avelar et al. |
| 2011/0270301 A1 | 11/2011 | Cornet et al. |
| 2011/0305736 A1 | 12/2011 | Wieland et al. |
| 2011/0319804 A1* | 12/2011 | Greener ............... A61F 15/001 83/13 |
| 2012/0016321 A1 | 1/2012 | Wu et al. |
| 2012/0029455 A1 | 2/2012 | Perez-Foullerat et al. |
| 2012/0059412 A1 | 3/2012 | Fleischmann |
| 2012/0130327 A1 | 5/2012 | Marquez |
| 2012/0136326 A1 | 5/2012 | Croizat et al. |
| 2012/0136328 A1 | 5/2012 | Johannison et al. |
| 2012/0143113 A1 | 6/2012 | Robinson et al. |
| 2012/0172926 A1 | 7/2012 | Hotter |
| 2012/0191132 A1 | 7/2012 | Sargeant |
| 2012/0209226 A1 | 8/2012 | Simmons et al. |
| 2012/0209227 A1* | 8/2012 | Dunn ..................... A61M 1/90 604/319 |
| 2012/0253302 A1 | 10/2012 | Corley |
| 2013/0023842 A1 | 1/2013 | Song |
| 2013/0150813 A1 | 6/2013 | Gordon et al. |
| 2013/0190705 A1 | 7/2013 | Vess et al. |
| 2013/0197457 A1 | 8/2013 | Kazala, Jr. et al. |
| 2013/0204213 A1 | 8/2013 | Heagle et al. |
| 2013/0245527 A1 | 9/2013 | Croizat et al. |
| 2013/0325142 A1 | 12/2013 | Hunter et al. |
| 2013/0331757 A1 | 12/2013 | Belson |
| 2014/0094730 A1 | 4/2014 | Greener et al. |
| 2014/0163415 A1 | 6/2014 | Zaiken et al. |
| 2014/0196736 A1 | 7/2014 | Fernando et al. |
| 2014/0249495 A1 | 9/2014 | Mumby et al. |
| 2015/0065968 A1 | 3/2015 | Sealy et al. |
| 2015/0119837 A1 | 4/2015 | Thompson, Jr. et al. |
| 2015/0157758 A1 | 6/2015 | Blücher et al. |
| 2015/0190288 A1 | 7/2015 | Dunn et al. |
| 2015/0196431 A1 | 7/2015 | Dunn et al. |
| 2015/0320602 A1 | 11/2015 | Locke et al. |
| 2015/0374561 A1 | 12/2015 | Hubbard, Jr. et al. |
| 2016/0144085 A1 | 5/2016 | Melin et al. |
| 2016/0184496 A1 | 6/2016 | Jaecklein et al. |
| 2017/0065751 A1 | 3/2017 | Toth et al. |
| 2017/0196736 A1* | 7/2017 | Long ................... A61F 13/0216 |
| 2017/0281838 A1 | 10/2017 | Dunn |

FOREIGN PATENT DOCUMENTS

| | | |
|---|---|---|
| CN | 101112326 A | 1/2008 |
| CN | 101744688 A | 6/2010 |
| CN | 201519362 U | 7/2010 |
| CN | 102038575 A | 5/2011 |
| CN | 202568632 U | 12/2012 |
| CN | 103071197 A | 5/2013 |
| CN | 203408163 U | 1/2014 |
| DE | 2949920 A1 | 3/1981 |
| EP | 1320342 A1 | 6/2003 |
| EP | 2279016 A1 | 2/2011 |
| EP | 2567717 A1 | 3/2013 |
| EP | 2601984 A2 | 6/2013 |
| GB | 2389794 A | 12/2003 |
| GB | 2423019 A | 8/2006 |
| GB | 2489947 A | 10/2012 |
| GB | 2496310 A | 5/2013 |
| JP | S62-57560 A | 3/1987 |
| JP | 2012-105840 A | 6/2012 |
| RU | 62504 U1 | 4/2007 |
| SU | 1818103 A1 | 5/1993 |
| WO | WO 01/85248 A1 | 11/2001 |
| WO | WO 01/89392 A2 | 11/2001 |
| WO | WO 02/05737 A1 | 1/2002 |
| WO | WO 03/003948 A1 | 1/2003 |
| WO | WO 03/049598 A2 | 6/2003 |
| WO | WO 2005/046761 A1 | 5/2005 |
| WO | WO 2005/105174 A1 | 11/2005 |
| WO | WO 2006/046060 A2 | 5/2006 |
| WO | WO 2008/027449 A2 | 3/2008 |
| WO | WO 2008/064502 A1 | 6/2008 |
| WO | WO 2008/104609 A1 | 9/2008 |
| WO | WO 2009/112062 A1 | 9/2009 |
| WO | WO 2010/033725 A2 | 3/2010 |
| WO | WO 2010/097570 A1 | 9/2010 |
| WO | WO 2011/023384 A1 | 3/2011 |
| WO | WO 2012/082716 A2 | 6/2012 |
| WO | WO 2012/082876 A1 | 6/2012 |
| WO | WO 2012/136707 A1 | 10/2012 |
| WO | WO 2012/142473 A1 | 10/2012 |
| WO | WO 2013/012381 A1 | 1/2013 |
| WO | WO 2013/043258 A1 | 3/2013 |
| WO | WO 2013/071243 A2 | 5/2013 |
| WO | WO 2013/076450 A1 | 5/2013 |
| WO | WO 2013/079947 A1 | 6/2013 |
| WO | WO 2013/175309 A1 | 11/2013 |
| WO | WO 2013/175310 A2 | 11/2013 |
| WO | WO 2014/013348 A2 | 1/2014 |
| WO | WO 2014/024048 A1 | 2/2014 |
| WO | WO 2014/140578 A1 | 9/2014 |
| WO | WO 2014/158526 A1 | 10/2014 |
| WO | WO 2014/165275 A1 | 10/2014 |
| WO | WO 2014/178945 A1 | 11/2014 |
| WO | WO 2014/194786 A1 | 12/2014 |
| WO | WO 2015/008054 A1 | 1/2015 |
| WO | WO 2015/061352 A2 | 4/2015 |
| WO | WO 2015/109359 A1 | 7/2015 |
| WO | WO 2015/110409 A1 | 7/2015 |
| WO | WO 2015/110410 A1 | 7/2015 |
| WO | WO-2015110409 A1 * | 7/2015 ....... A61F 13/00068 |
| WO | WO 2015/169637 A1 | 11/2015 |
| WO | WO 2015/193257 A | 12/2015 |
| WO | WO 2016/018448 A1 | 2/2016 |
| WO | WO 2016/176513 A1 | 11/2016 |
| WO | WO 2016/179245 A1 | 11/2016 |
| WO | WO 2017/106576 A1 | 6/2017 |
| WO | WO 2018/038665 A1 | 3/2018 |
| WO | WO 2018/041805 A1 | 3/2018 |
| WO | WO 2018/044949 A1 | 3/2018 |
| WO | WO 2018/085457 A1 | 5/2018 |
| WO | WO-2018108785 A1 | 6/2018 |
| WO | WO 2018/140386 A2 | 8/2018 |
| WO | WO-2018229009 A1 | 12/2018 |
| WO | WO-2018229010 A1 | 12/2018 |
| WO | WO-2018229012 A1 | 12/2018 |

OTHER PUBLICATIONS

"Definition of 3D Printer," American Heritage Dictionary of the English Language, Fifth Edition, accessed on Feb. 22, 2018 from URL: https://www.thefreedictionary.co, 2016, 1 page.

"Definition of Adhere," The Free Dictionary, accessed on Mar. 23, 2017 from http://www.thefreedictionary.com/adhere, 6 pages.

"Definition of Oculiform," Webster's Revised Unabridged Dictionary, accessed from the Free Dictionary on May 30, 2018 from URL: https://www.thefreedictionary.com/Oculiform, 1913, 1 page.

"Definition of Throughout," Merriam-Webster Dictionary, accessed on Aug. 29, 2017 from https://www.merriam-webster.com/dictionary/throughout, 11 pages.

(56) References Cited

OTHER PUBLICATIONS

Hougaard, et al., "The Open Abdomen: Temporary Closure with a Modified Negative Pressure Therapy Technique," International Wound Journal, ISSN 1742-4801,2014, pp. 13-16.
Kapischke M., et al., "Self-Fixating Mesh for the Lichtenstein Procedure—a Prestudy," Langenbecks Arch Surg, 2010, vol. 395, pp. 317-322.
International Preliminary Report on Patentability for Application No. PCT/EP2018/069871, dated Feb. 6, 2020, 9 pages.

* cited by examiner

6500

Length

Length

CUSTOMIZABLE WOUND CLOSURE DEVICE AND METHOD OF USE

CROSS-REFERENCE TO RELATED APPLICATIONS

This application is a U.S. national stage application of International Patent Application No. PCT/EP2018/069871, filed Jul. 23, 2018, which claims priority to U.S. Provisional Patent Application No. 62/537,617, filed on Jul. 27, 2017 each of which is incorporated by reference herein in its entirety.

BACKGROUND

Field

This application describes embodiments of apparatuses, methods, and systems for the treatment of wounds, specifically to aid in the closure of large wounds, in conjunction with the administration of negative pressure.

Description of the Related Art

Negative pressure wound therapy has been used in the treatment of wounds, and in many cases can improve the rate of healing while also removing exudates and other deleterious substances from the wound site.

Abdominal compartment syndrome is caused by fluid accumulation in the peritoneal space due to edema and other such causes, and results in greatly increased intra-abdominal pressure that may cause organ failure eventually resulting in death. Causes may include sepsis or severe trauma. Treatment of abdominal compartment syndrome may require an abdominal incision to permit decompression of the abdominal space, and as such, a large wound may be created onto the patient. Closure of this wound, while minimizing the risk of secondary infections and other complications, and after the underlying edema has subsided, then becomes a priority. However, acute open abdominal conditions may be caused by other reasons in addition to compartment syndrome, as described further below.

Other large or incisional wounds, either as a result of surgery, trauma, or other conditions, may also require closure. For example, wounds resulting from sternotomies, fasciotomies, and other abdominal wounds may require closure. Wound dehiscence of existing wounds is another complication that may arise, possibly due to incomplete underlying fascial closure, or secondary factors such as infection.

Existing negative pressure treatment systems, while permitting eventual wound closure, still require lengthy closure times. Although these may be combined with other tissue securement means, such as sutures, there is also a risk that underlying muscular and fascial tissue is not appropriately reapproximated so as to permit complete wound closure. Further, when foam or other wound fillers are inserted into the wound, the application of negative pressure to the wound and the foam may cause atmospheric pressure to bear down onto the wound, compressing the foam downward and outward against the margins of the wound. This downward compression of the wound filler slows the healing process and slows or prevents the joining of wound margins. Additionally, inflammation of the fascia in the form of certain types of fasciitis can lead to rapid and excessive tissue loss, potentially meriting the need for more advanced negative pressure treatment systems.

Further, because wounds are of different shapes and/or sizes, foam or other wound fillers may need to be sized or shaped to better accommodate wounds. Although existing foam or other wound fillers may be cut or tear to certain size or shape, the adjustment may be limited by various factors, such as the size or the shape of the original foam or other wound fillers. Additionally, a wound may change its size or shape as negative pressure treatment continues. Accordingly, there is a need to provide for an improved apparatus, method, and system for the treatment and closure of wounds.

SUMMARY

Embodiments of the present invention relate to negative pressure wound closure devices, methods of making the same, and methods and systems that facilitate closure of a wound. It will be understood by one of skill in the art that the wounds described herein this specification may encompass any wound, and are not limited to a particular location or type of wound. The devices, methods, and systems may operate to reduce the need for repetitive replacement of wound filler material currently employed and can advance the rate of healing. The devices, methods, and systems may be simultaneously used with negative pressure to remove wound fluids.

In some embodiments, a wound closure device may comprise a plurality of building blocks and/or building units configured to be adhered to or attached to each other to form an assembled structure for insertion into or placement over a wound.

In some embodiments, each of the building blocks and/or building units may comprise at least one cell. The building blocks and/or building units may be configured to form an assembled stabilizing structure comprising a plurality of cells defined by one or more walls, wherein in the assembled stabilizing structure cells are provided side-by-side in a horizontal plane and each of the cells has a top end and a bottom end with an opening extending through the top and bottom ends.

In some embodiments, the plurality of building blocks and/or building units may be configured to be reversibly adhered to one another. One or more of the building blocks and/or building units may comprise attachment elements and/or receiving elements configured to receive attachment elements of one or more of the building blocks and/or building units.

In some embodiments, one or more of the building blocks and/or building units may have an elongate shape with a uniform width. Each building units may comprise one or more cells provided in a single row. Each of building units may have a uniform width. Each of the building units may be configured to reduce or increase its length by removing or adding cells respectively.

In some embodiments, each of the building blocks and/or building units may comprise cells having a uniform shape and size. Each of one or more building blocks may consist of one cell. Each of the building blocks and/or building units may comprise at least one cell having a triangular, quadrilateral or hexagonal shape.

In some embodiments, each of the building blocks and/or building units comprises foam or porous material. One or more building blocks and/or building units may further comprise precuts defining frangible portions of the foam or porous material. One or more of the plurality of building blocks and/or building units may be configured to be cut or torn.

In some embodiments, the wound closure device may further comprise a source of negative pressure, a drape and/or an organ protection layer. The wound closure device may further comprise a port configured to transmit negative pressure through a drape placed over the wound.

In certain embodiments, a method of treating a wound comprises:
adhering a plurality of building blocks and/or building units to one another to provide a stabilizing structure;
inserting the stabilizing structure into the wound;
wherein the plurality of building blocks and/or building units comprise one or more cells,
wherein the plurality of building blocks and/or building units are configured to be adhered to one another to provide the stabilizing structure.

In some embodiments, the method may further comprise adjusting the size and/or shape of the building blocks and/or the building units, optionally by detaching one or more cells from one or more units, wherein one or more units have two or more cells. The method may further comprise providing a plurality of building units having a uniform size and shape, and subsequently adjusting the size and/or shape of each of the plurality of building units having the uniform size and shape. The method may further comprise detaching one or more building blocks and/or the building units from the stabilizing structure, wherein the plurality of building blocks and/or the building units are detachably adhered.

In some embodiments, the method may further comprise covering the stabilizing structure with a drape sealed to skin surrounding the wound; and applying negative pressure through the drape to the wound via a source of negative pressure, wherein the application of negative pressure causes the stabilizing structure to horizontally collapse. The method may further comprise inserting a tissue protection layer over the wound before inserting the stabilizing structure.

Other embodiments of wound closure devices, stabilizing structures and associated apparatuses and methods are described below.

BRIEF DESCRIPTION OF THE DRAWINGS

Other features and advantages of the present invention will be apparent from the following detailed description of the invention, taken in conjunction with the accompanying drawings of which.

DETAILED DESCRIPTION

Figure 1:
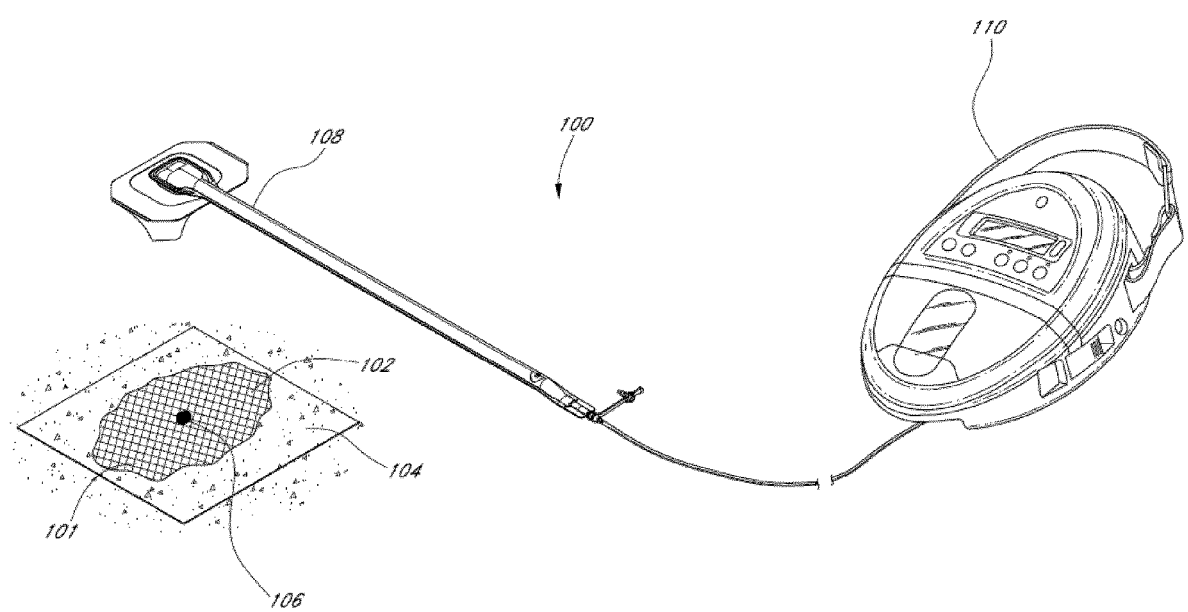
FIG. 1 illustrates an embodiment of a negative pressure treatment system.

Embodiments disclosed in this section or elsewhere in this specification relate to apparatuses and methods of treating a wound with reduced pressure, including pump and wound dressing components and apparatuses. The apparatuses and components comprising the wound overlay and packing materials, if any, are sometimes collectively referred to in this section or elsewhere in this specification as dressings.

It will be appreciated that throughout this specification reference is made to a wound. It is to be understood that the term wound is to be broadly construed and encompasses open and closed wounds in which skin is torn, cut or punctured or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, abdominal wounds or other large or incisional wounds, either as a result of surgery, trauma, sternotomies, fasciotomies, or other conditions, dehisced wounds, acute wounds, chronic wounds, subacute and dehisced wounds, traumatic wounds, flaps and skin grafts, lacerations, abrasions, contusions, burns, electrical burns, diabetic ulcers, pressure ulcers, stoma, surgical wounds, trauma and venous ulcers or the like.

As is used in this section or elsewhere in this specification, reduced or negative pressure levels, such as −X mmHg, represent pressure levels that are below standard atmospheric pressure, which corresponds to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg. In addition, negative pressure that is "less" or "smaller" than −X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg).

The negative pressure range for some embodiments of the present disclosure can be approximately −80 mmHg, or between about −10 mmHg and −200 mmHg Note that these pressures are relative to normal ambient atmospheric pressure. Thus, −200 mmHg would be about 560 mmHg in practical terms. In some embodiments, the pressure range can be between about −40 mmHg and −150 mmHg. Alternatively, a pressure range of up to −75 mmHg, up to −80 mmHg or over −80 mmHg can be used. Also in other embodiments a pressure range of below −75 mmHg can be used. Alternatively, a pressure range of over approximately −100 mmHg, or even −150 mmHg, can be supplied by the negative pressure apparatus. In some embodiments, the negative pressure range can be as small as about −20 mmHg or about −25 mmHg, which may be useful to reduce fistulas. In some embodiments of wound closure devices described here, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. In some embodiments, negative pressure may be varied over time for example using a sinusoidal wave, square wave, and/or in synchronization with one or more patient physiological indices (e.g., heartbeat).

Examples of such applications where additional disclosure relating to the preceding descriptions may be found include U.S. Pat. No. 8,235,955, titled "Wound treatment apparatus and method," issued Aug. 7, 2012 and U.S. Pat. No. 7,753,894, titled "Wound cleansing apparatus with stress," issued Jul. 13, 2010. Both applications are hereby incorporated by reference in their entirety. Other applications that may contain teachings relevant for use with the embodiments described in this section or elsewhere in this specification may include application Ser. No. 12/886,088, titled "Systems And Methods For Using Negative Pressure Wound Therapy To Manage Open Abdominal Wounds," filed Sep. 20, 2010, published as US 2011/0213287; application Ser. No. 13/092,042, titled "Wound Dressing And Method Of Use," filed Apr. 21, 2011, published as US 2011/0282309; and application Ser. No. 13/365,615, titled "Negative Pressure Wound Closure Device," filed Feb. 3, 2012, published as US 2012/0209227, the entireties of each of which are hereby incorporated by reference. Still more applications that may contain teachings relevant for use with the embodiments described in this specification are application Ser. No. 13/942,493, titled "Negative Pressure Wound Closure Device," filed Jul. 15, 2013, published as US 2014/0180225; PCT App. No. PCT/US2013/050619, filed Jul. 16, 2013 titled "Negative Pressure Wound Closure Device," published as WO 2014/014871 A1; PCT App. No. PCT/US2013/050698, filed Jul. 16, 2013 titled "Negative Pressure Wound Closure Device," published as WO 2014/014922 A1; PCT App. No. PCT/IB2013/01555, titled "Devices and Methods for Treating and Closing Wounds with Negative Pressure," filed May 5, 2013, published as WO 2013/175309 A1; PCT App. No. PCT/US2014/025059, titled "Negative Pressure Wound Closure Device and Systems and Methods of Use in Treating Wounds with Negative Pressure," filed Mar. 12, 2014, published as WO 2014/165275 A1; and PCT App. No. PCT/GB2014/050746, "Compressible Wound Fillers and Systems and Methods of Use In Treating Wounds With Negative Pressure," filed Mar. 13, 2014, published as WO 2014/140578 A1, and "Negative Pressure Wound Closure Device," filed Oct. 21, 2014, and published as PCT/US2014/061627. The entireties of the aforementioned applications are each hereby incorporated by reference and should be considered part of the present specification.

It will be understood that throughout this specification, in some embodiments, reference is made to an elongate, elongated or longitudinal strip or strips. It is to be understood that these terms are to be broadly construed and refer in some embodiments to an elongate material having two parallel or substantially parallel faces, where in cross-section a thickness of the material as measured perpendicular to the faces is relatively smaller than a height of the material measured parallel to the faces. While in some embodiments the strips may be constructed from discrete lengths of material, in other embodiments the strips may simply refer to elongate portions of an overall structure having two parallel or substantially parallel faces. The strips in some embodiments have a rectangular or generally rectangular-shaped faces, wherein a length of the face is longer than the height of the face. In some embodiments, the length of the face may be more than 2 times, 4 times, 6 times, 8 time, 10 times, 12 times or more greater than the height of the face.

As used in this section or elsewhere in this specification, the term "horizontal," when referring to a wound, indicates a direction or plane generally parallel to the skin surrounding the wound. The term "vertical," when referring to a wound, generally refers to a direction extending perpendicular to the horizontal plane. The term "longitudinal," when referring to a wound, generally refers to a direction in the horizontal plane taken in a direction along which the wound is longest. The term "lateral," when referring to a wound, generally refers to a direction in the horizontal plane perpendicular to the longitudinal direction. The terms "horizontal," "vertical," "longitudinal" and "lateral" may also be used to describe the stabilizing structures and wound closure devices described throughout this specification. When describing these structures or devices, these terms should not be construed to require that the structures or devices necessarily be placed into a wound in a certain orientation, though in certain embodiments, it may be preferable to do so.

FIG. 1 illustrates an embodiment of a negative pressure treatment system 100 that comprises a wound packer 102 inserted into a wound 101. The wound packer 102 may comprise porous materials such as foam, and in some embodiments, may comprise one or more embodiments of wound closure devices described in further detail in this section or elsewhere in this specification. In some embodiments, the perimeter or top of any wound closure device inserted into the wound 101 may also be covered with foam or other porous materials. A single drape 104 or multiple drapes may be placed over the wound 101, and is preferably adhered or sealed to the skin on the periphery of the wound 101 so as to create a fluid-tight seal. An aperture 106 may be made through the drape 104 which can be manually made or preformed into the drape 104 so as to provide a fluidic connection from the wound 101 to a source of negative pressure such as a pump 110. Preferably, the fluidic connection between the aperture 106 and the pump 110 is made via a conduit 108. In some embodiments, the conduit 108 may comprise a RENASYS® Soft Port™, manufactured by Smith & Nephew. Of course, in some embodiments, the drape 104 may not necessarily comprise an aperture 106, and the fluidic connection to the pump 110 may be made by placing the conduit 108 below the drape. In some wounds, particularly larger wounds, multiple conduits 108 may be used, fluidically connected via one or more apertures 106.

In some embodiments, the drape 104 may be provided with one or more corrugations or folds. Preferably, the corrugations are aligned along the longitudinal axis of the wound, and as such may support closure of the wound by preferentially collapsing in a direction perpendicular to the longitudinal axis of the wound. Such corrugations may aid in the application of contractile forces parallel to the wound surface and in the direction of wound closure. Examples of such drapes may be found in application Ser. No. 12/922,118, titled "Vacuum Closure Device," filed Nov. 17, 2010 (published as US 2011/0054365), which is hereby incorporated by reference in its entirety.

In use, the wound 101 is prepared and cleaned. In some cases, such as abdominal wounds, a non- or minimally-adherent organ protection layer (not illustrated) may be applied over any exposed viscera. The wound packer 102 is then inserted into the wound, and is covered with the drape 104 so as to form a fluid-tight seal. A first end of the conduit 108 is then placed in fluidic communication with the wound, for example via the aperture 106. The second end of the conduit 108 is connected to the pump 110. The pump 110 may then be activated so as to supply negative pressure to the wound 101 and evacuate wound exudate from the wound 101. As will be described in additional detail below and in relation to the embodiments of the foregoing wound closure devices, negative pressure may also aid in promoting closure of the wound 101, for example by approximating opposing wound margins.

Any structure or component disclosed herein this section or elsewhere in the specification may comprise a radiopaque material. A radiopaque material advantageously allows a clinician to more easily find pieces of the wound closure device that may have come loose from the structure and become lost in the wound. Some examples of radiopaque materials include barium sulfate, bismuth trioxide, bismuth subcarbonate, bismuth oxychloride, and tungsten.

Figure 2:
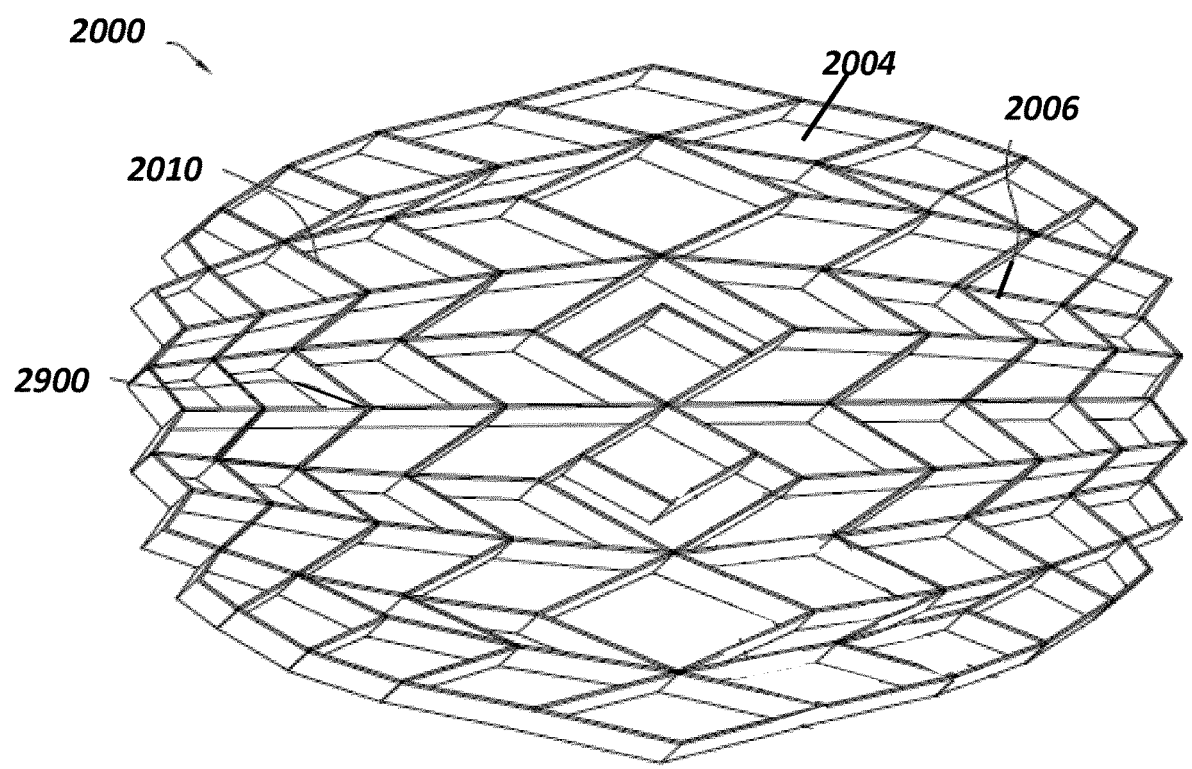
FIG. 2 illustrates an embodiment of a stabilizing structure.

Stabilizing Structures and Wound Closure Devices of FIG. 2

FIG. 2 is a drawing of an embodiment of a stabilizing structure 2000 comprising a plurality of elongate strips 2006 arranged in parallel or semi-parallel, whose longitudinal length can be aligned with the longitudinal axis of a wound. In embodiments, the elongate strips 2006 may also be arranged in a non-parallel fashion. The various cells within this stabilizing structure 2000 may have a variety of shapes and sizes. As will be described in greater detail below, the length and shape of the elongate strips 2006, intervening members 2010, and cells 2004 may be designed so as to facilitate greater closure of the stabilizing structure. In certain embodiments, the junctions 2900 between the elongate strips and intervening members may be thinned to better facilitate rotation and closure of the stabilizing structures. In some embodiments, the stabilizing structure is tearable, such that the structure may be shaped into the shape of a wound. As described elsewhere in the specification, tears may be completed at the intersections between intervening members and elongate strips or at any suitable location along the elongate strip or intervening member.

In some embodiments, the stabilizing structure 2000 may have an outer perimeter that defines an at least partially elliptical shape. Advantageously, the elliptical shape of stabilizing structure 2000 may allow the structure to better accommodate the shape of the wound. Most wounds are in shapes that are rounded, thus, an elliptically shaped stabilizing structure 2000 may better fit into a wound.

As described above, the stabilizing structure 2000 may comprise a plurality of cells 2004 provided side-by-side, each cell defined by one or more walls, each cell having a top end and a bottom end with an opening extending through the top and bottom ends. As with the other stabilizing structures described herein this section and elsewhere in the specification, the stabilizing structure 2000 is configured to collapse by collapsing one or more cells 2004. In some embodiments, the cells are all of the same approximate shape and size; however, in other embodiments, the cells are of different shapes and sizes. In some embodiments, the stabilizing structures as described herein this section or elsewhere in the specification may be domed, such that the central portion of the stabilizing structure bulges upward. For example, a lower portion of the stabilizing structure may be concave, while an upper portion of the stabilizing structure is convex.

In certain embodiments, the stabilizing structure 2000 can collapse in any manner described in this section or elsewhere in this specification with or without the application of negative pressure. For example, the stabilizing structure may collapse significantly more in one plane than in another plane upon application of negative pressure. In some embodiments, the stabilizing structure is configured to collapse more in a horizontal plane parallel to the length and width of the stabilizing structure than in a vertical plane perpendicular to the horizontal plane. In embodiments, particular rows may collapse in a first direction, while another row may collapse in the same or an opposing direction. In certain embodiments, the stabilizing structure may collapse along the width of the stabilizing structure while remaining relatively rigid along the length of the stabilizing structure and in the vertical direction.

The stabilizing structure may be comprised of any materials described in this section or elsewhere in this specification, including: flexible plastics such as silicone, polyurethane, rigid plastics such as polyvinyl chloride, semi-rigid plastics, semi-flexible plastics, biocompatible materials, composite materials, metals, and foam. In certain embodiments, the stabilizing structure may comprise a radio opaque material, to more readily allow a clinician to find pieces of the stabilizing structure within the wound.

The stabilizing structure 2000 and all stabilizing structures and wound closure devices described in this section or elsewhere in this specification can collapse on a variety of timescales in a dynamic fashion. In certain embodiments, the majority of the collapse may occur within the first few minutes upon application of negative pressure. However, after the initial collapse, the stabilizing structure or wound closure device may continue to collapse at a much slower rate, thereby applying increasing longitudinal tension over a long period of time and drawing the edges of the wound closer together. By slowly drawing the wound edges closer together over time, the stabilizing structure or wound closure device allows the surrounding healing tissue to remodel synergistically with the closure of the device or stabilizing structure. Slow, dynamic wound closure may allow the surrounding tissue to heal at an accelerated rate, because the collapsing structure or device slowly brings the edges of the wound closer together without stressing the newly formed or weakened tissue too quickly.

In some embodiments, the stabilizing structures described in this section or elsewhere in this specification can be placed into a wound for a period of time and then removed or replaced with another stabilizing structure. For example, a stabilizing structure could be inserted into a wound for a period of time, promoting closure of the wound by drawing the edges closer together. After a period of time has passed, the stabilizing structure can be replaced by a stabilizing structure of a different size or collapsibility, for example a stabilizing structure of a smaller size or decreased density. This process could be repeated over and over, thereby continuously drawing the edges of the wound together over time and allowing for continuing repair and remodeling of the surrounding tissue. In certain embodiments, the stabilizing structure is configured to remain in the wound for at least about less than 1 hour, at least about 1 hour, at least about 2 hours, at least about 4 hours, at least about 6 hours, at least about 8 hours, at least about 12 hours, at least about 24 hours, at least about 2 days, at least about 4 days, at least about 6 days, at least about 1 week, at least about 2 weeks, at least about 3 weeks, or more than 3 weeks.

In certain embodiments, up to 90% of the collapse of the stabilizing structure or wound closure device may occur within the first few minutes upon application of negative pressure, while the remaining 10% of the collapse may occur slowly over a period of many minutes, hours, days, weeks, or months. In other embodiments, up to about 80% of the collapse, up to about 70%, up to about 60%, up to about 50%, up to about 40%, up to about 30%, up to about 20%, up to about 10%, or about 0% of the collapse will occur immediately within the first few minutes upon application of negative pressure while the remainder of the collapse occurs at a much slower rate such as over the course of many minutes, hours, days weeks, or months. In other embodiments, the stabilizing structure can collapse at a variable rate. In some embodiments, the entirety of the collapse occurs at a slowed rate, while in other embodiments the entirety of the collapse occurs almost immediately within the first few minutes. In further embodiments, the collapse can occur at any rate and the rate can vary over time. In certain embodiments, the rate of collapse can be altered in a variable fashion by adding and/or removing portions of the structure or by controlling the application of negative pressure and irrigant fluid.

In some embodiments, the stabilizing structure 2000 of FIG. 2 can be configured to include perforations or detachable sections that allow portions of the device to separate from the remainder of the device. For example, perforations may be incorporated into the joints 2900 between various cells 2004 contained within the stabilizing structure 2000, allowing for the removal of individual rows or cells to alter the shape of the stabilizing structure 2000.

Applicable to all stabilizing structures or wound closure devices described in this section or elsewhere in the specification, the stabilizing structure or wound closure device may be tearable such that the stabilizing structure may be shaped into the shape of a wound. In some embodiments, the stabilizing structure may be torn at the intersections between intervening members and elongate strips, while in further embodiments, the elongate strips or intervening members may be torn at any suitable position.

Wound Closure and Treatment Methods of FIGS. 3-10G

The stabilizing structures and/or wound closure devices described in this section or elsewhere in this specification may be used in conjunction with methods or systems for the closure of a wound. In some embodiments of methods of use for closure of a wound, one or more of the stabilizing structures or wound closure devices of any of the embodiments described in this section or elsewhere in this specification is placed into a wound. In some embodiments, an organ protection layer may be provided in the wound before placement of the stabilizing structure. In certain embodiments, foam or other porous material may be placed in the wound along with the stabilizing structure or wound closure device, either below, above, or surrounding the stabilizing structure or wound closure device. Foam or other porous material may also surround the perimeter of the stabilizing structure or wound closure device. The stabilizing structure or wound closure device may be configured to collapse in any manner as described in this section or elsewhere in this specification, for example by having a particular size and shape, or by comprising a certain volume of foam or other porous material within the cells of the structure. The stabilizing structure or wound closure device may further be altered in any manner described in this section or elsewhere in this specification so as to better accommodate the shape of the wound. After placement in the wound, the stabilizing structure or wound closure device can be sealed by a fluid-tight drape. The fluid-tight drape can comprise a port configured for the application of negative pressure. A source of negative pressure may then be connected to the port and negative pressure may be applied to the wound. The stabilizing structure or wound closure device may be replaced over time by stabilizing structures or wound closure devices of various shapes and sizes as desired to best promote wound healing.

FIGS. 3-10G are photographs and illustrations depicting embodiments of methods for the treatment of a wound that utilize a wound closure device comprising a stabilizing structure as described herein this section and elsewhere in the specification. To better illustrate non-limiting embodiments of the methods, numbers have been added to the steps of FIG. 10 to allow the reader to more easily follow these steps of the method. However, the steps can be performed in any order, and any numbering system is for clarity only. Further, in some embodiments, different steps of these methods may be excluded. In other embodiments, additional steps may be added to the methods based on methods described herein this section and elsewhere in the specification. The porous layers and structures described in this section may be of any material or structure described elsewhere in the specification, such as foam.

Figure 3:
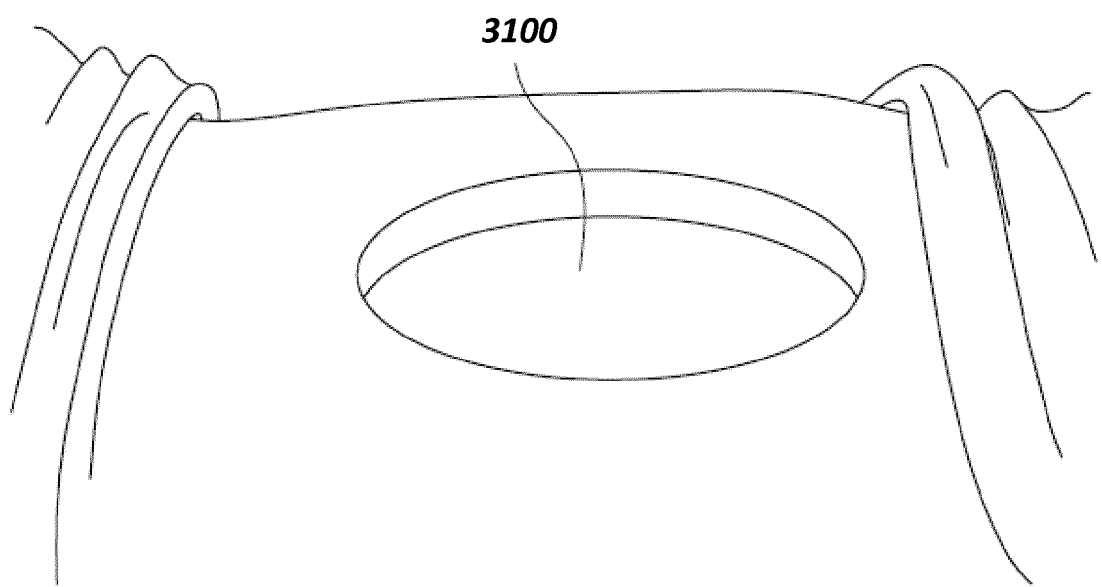
FIG. 3 illustrates an embodiment of an open abdominal wound.

FIG. 3 depicts an embodiment of an open wound 3100 prior to treatment with a wound closure device as will be described in much greater detail below. The open wound of FIG. 3 is similar to the wounds described elsewhere in the specification, particularly as relate to FIG. 1. In some instances, as described elsewhere in the specification, such a wound may be produced via a surgical incision or other means.

Figure 4:
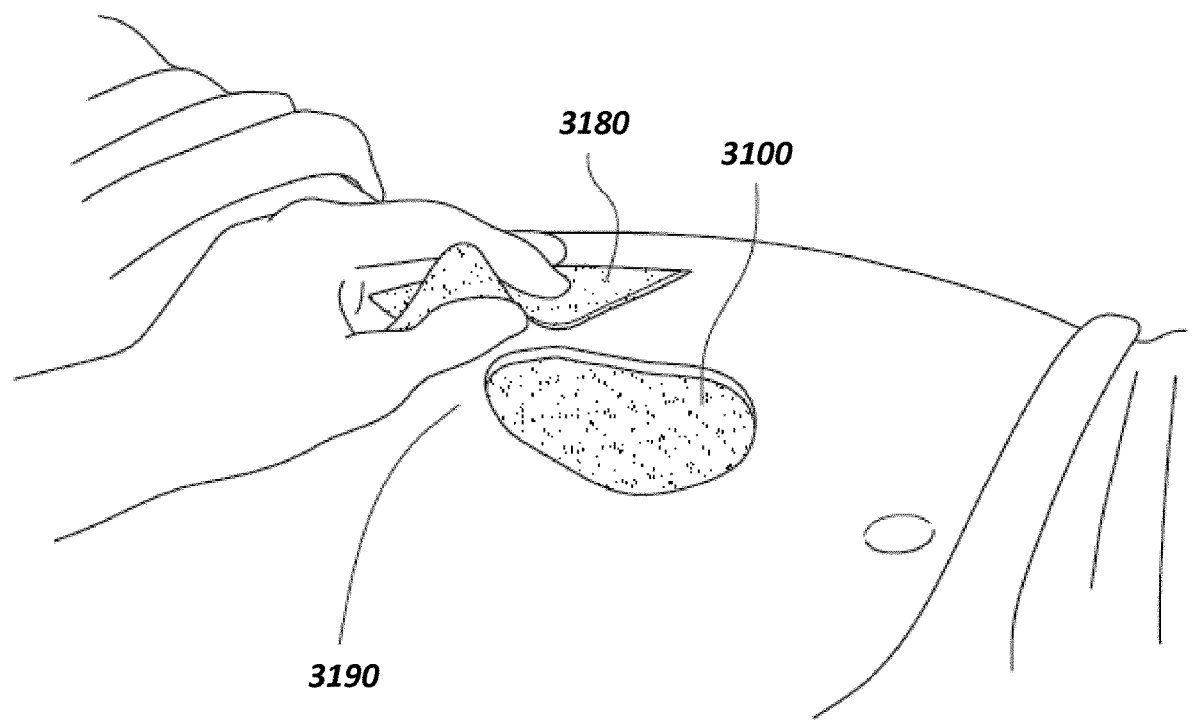
FIG. 4 illustrates an embodiment of a step in a method of treating a wound.

FIG. 4 depicts an embodiment of an initial step in a method for the treatment of an open wound 3100 with a wound closure device. Before treatment, the wound may be cleaned with a pad 3180 and the skin 3190 prepared for application of a wound closure device, such as those described in relation to FIG. 2.

Figure 5:
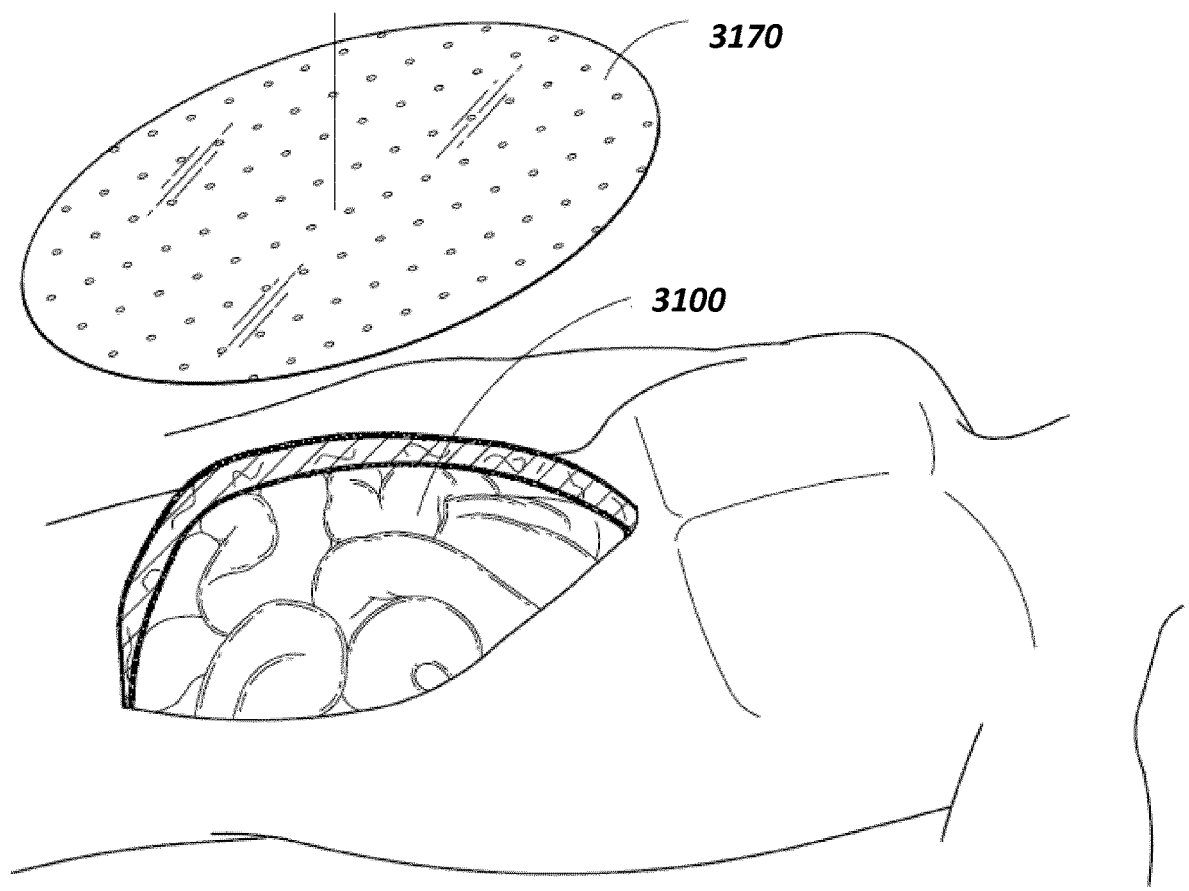
FIG. 5 illustrates an embodiment of a step in a method of treating a wound.

FIG. 5 depicts an embodiment of an early step in a method for the treatment of an open wound 3100. In some embodiments, a tissue protection layer 3170 may be placed over the wound to protect the underlying tissues from the rigors of negative pressure wound therapy or other potential harms. Accordingly, certain embodiments provide for a tissue protection layer 3170 which may be cut to size to be placed over the wound site 3100. The tissue protection layer 3170 can be a material which will not adhere to the wound site or to the exposed viscera in close proximity. Such a tissue protection layer may be constructed from any suitable material such as a biocompatible polymer. For example, organ protection layers manufactured by Smith & Nephew and sold under the brand RENASYS® may act as tissue protection layers and be placed over the abdominal cavity and/or wound bed 3100 and tucked over the peritoneal gutter. In further examples, materials such as the fluoropolymer polytetrafluoroethylene (PTFE) may be applicable as these materials are generally non-adherent and used in surgical grafts. In one embodiment, the tissue protection layer is permeable. For example, the tissue protection layer 3170 can be provided with openings, such as holes, slits, or channels, to allow the removal of fluids from the wound site 3100 or the transmittal of negative pressure to the wound site 3100. In further embodiments, the tissue protection layer may be used over non-abdominal wounds on other areas of the body, such as the leg, arm, shoulder, or back. In certain embodiments, the tissue protection layer may comprise a sensor configured to measure pressures in and around the wound. For example, the sensor may be used to measure the level of negative pressure applied to the wound or to measure the pressure on the underlying organs beneath the abdominal wound.

Figure 6A:
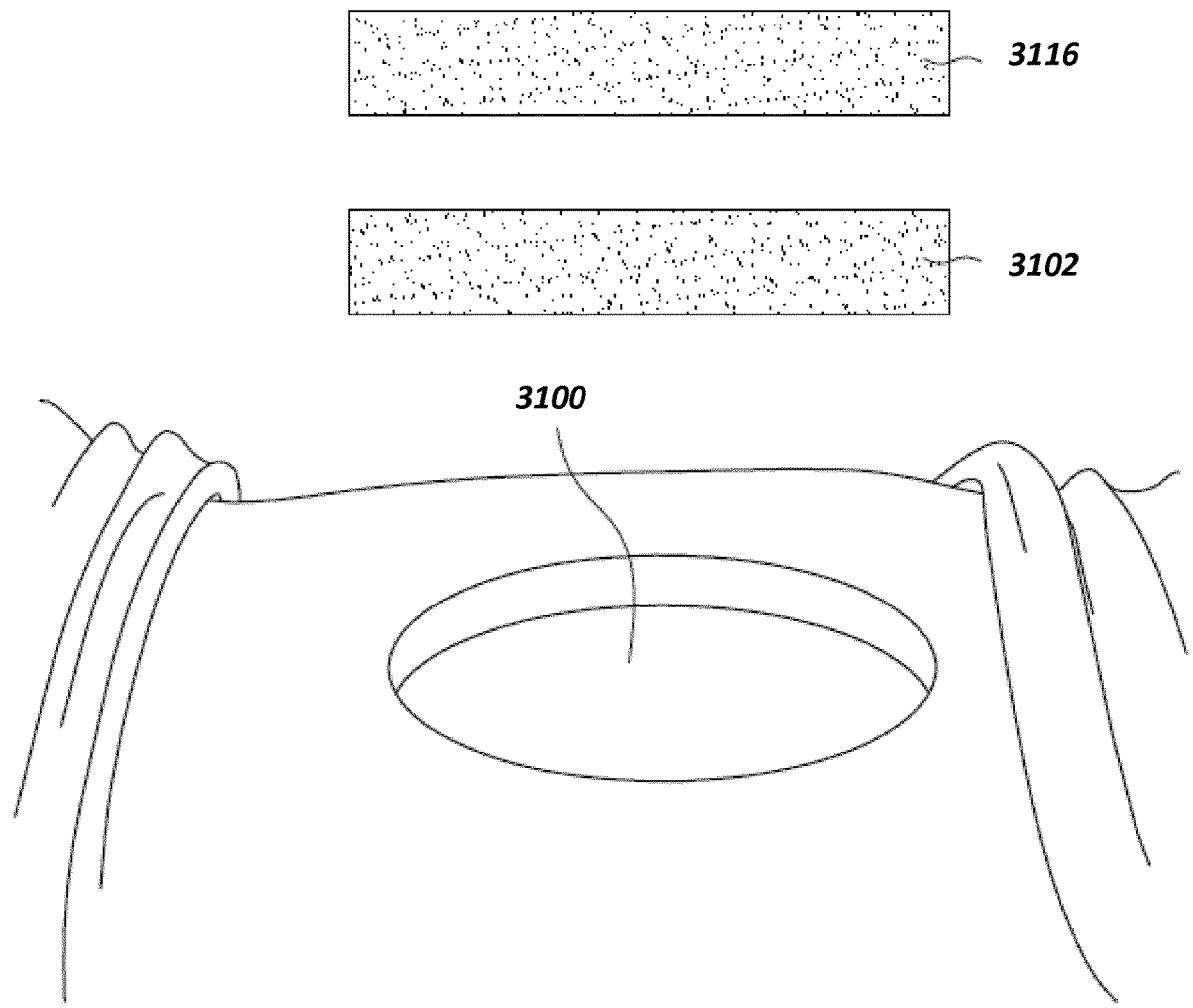
FIGS. 6A-B illustrate an embodiment of steps of a method of treating a wound.
Figure 6B:
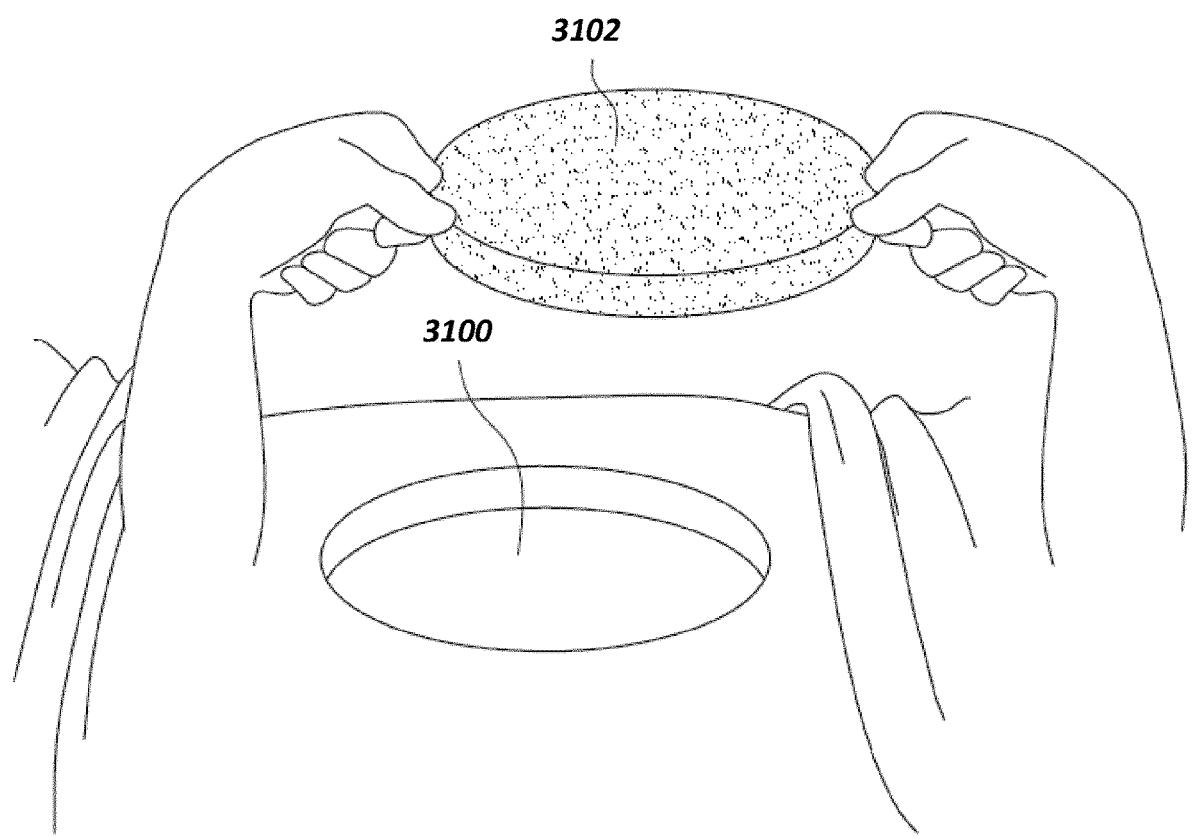

FIGS. 6A-B illustrate embodiments of possible initial steps in a method for the treatment of an open wound. However, as described above, the steps need not be performed in this order and may be performed in any order. In FIG. 6A, two pieces of a porous material such as foam, a bottom piece 3102 and a top piece 3116 are selected so as to approximate the size of the wound 3100. In some embodiments, the top piece and the bottom piece are of identical thickness. However, in certain embodiments, and vice-versa, top piece 3116 may be at least twice as thick, at least four times as thick, at least 10 times as thick or more than ten times as thick as bottom piece 3102. Bottom piece 3102 may be shaped via cutting or other suitable means to the shape of the wound and subsequently placed into the wound 3100, as shown in FIG. 6B and depicted further below in FIGS. 7A-B.

Figure 7A:
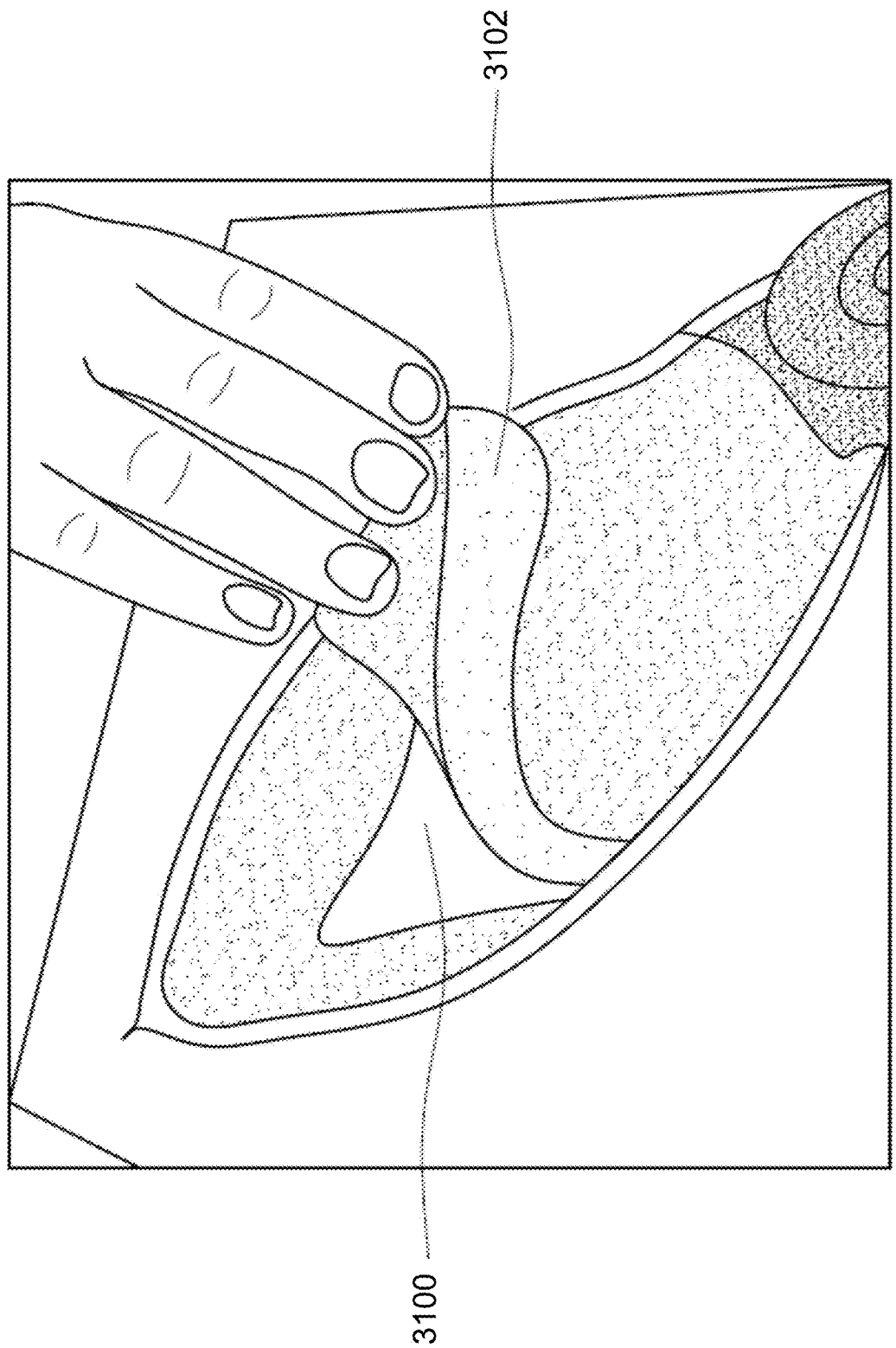
FIGS. 7A-B are photographs of steps of a method of treating a wound.
Figure 7B:
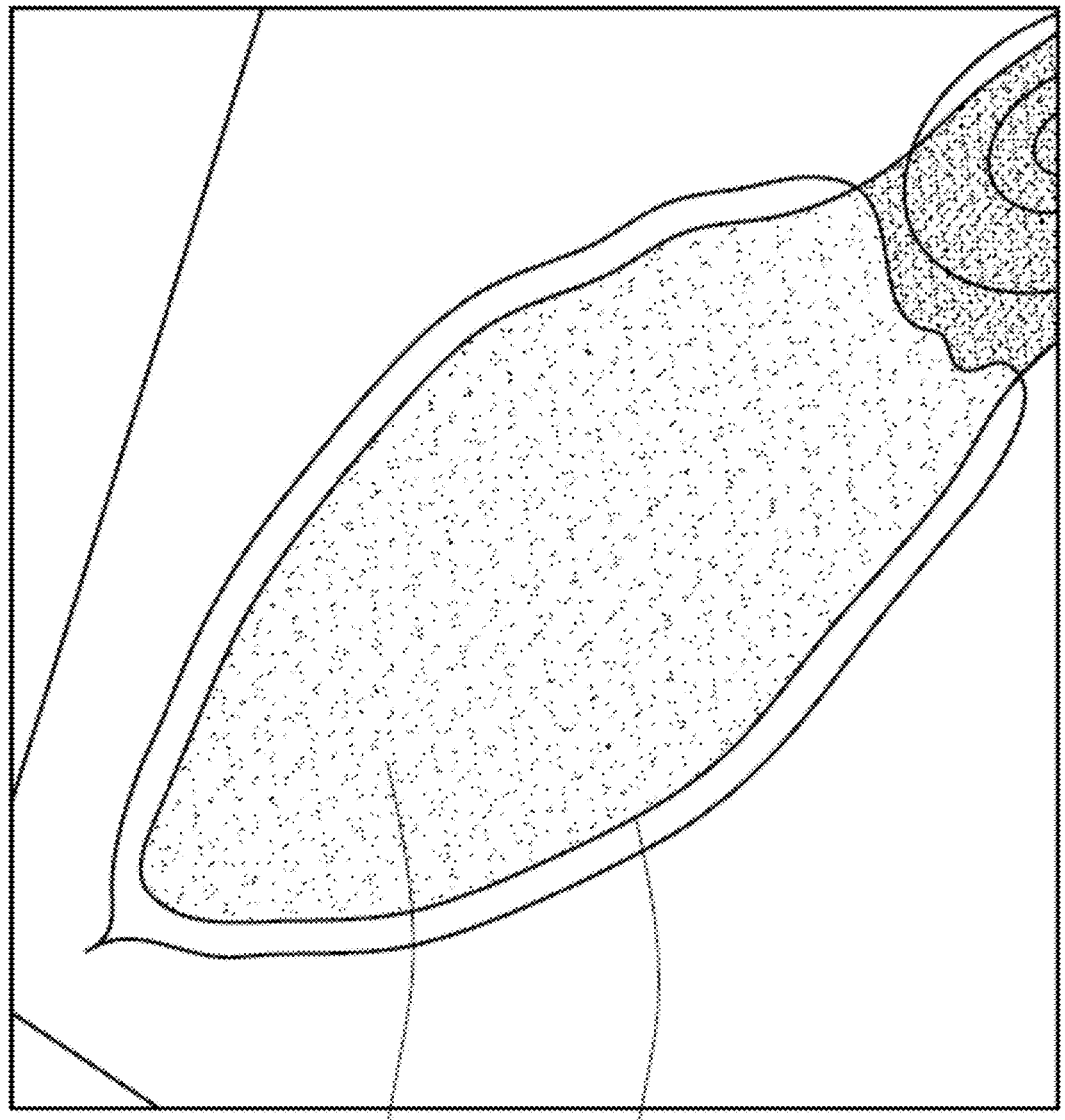
Figure 8A:
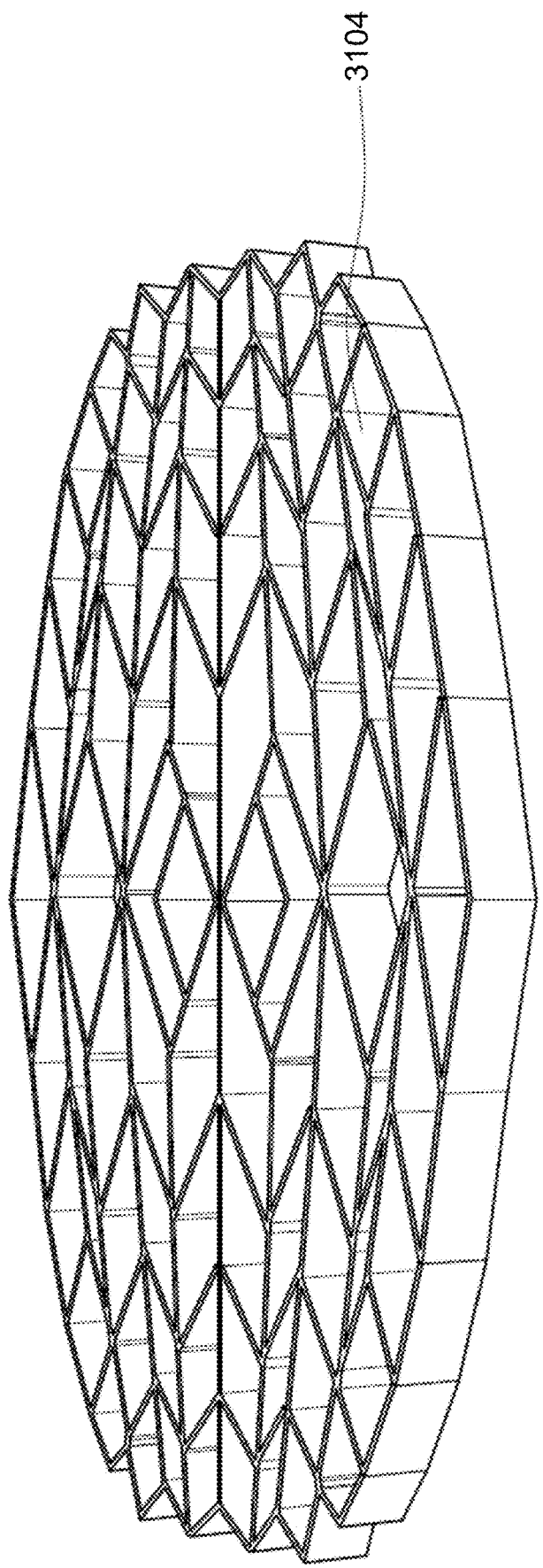
FIGS. 8A-C depict an embodiment of steps of a method of treating a wound.
Figure 8B:
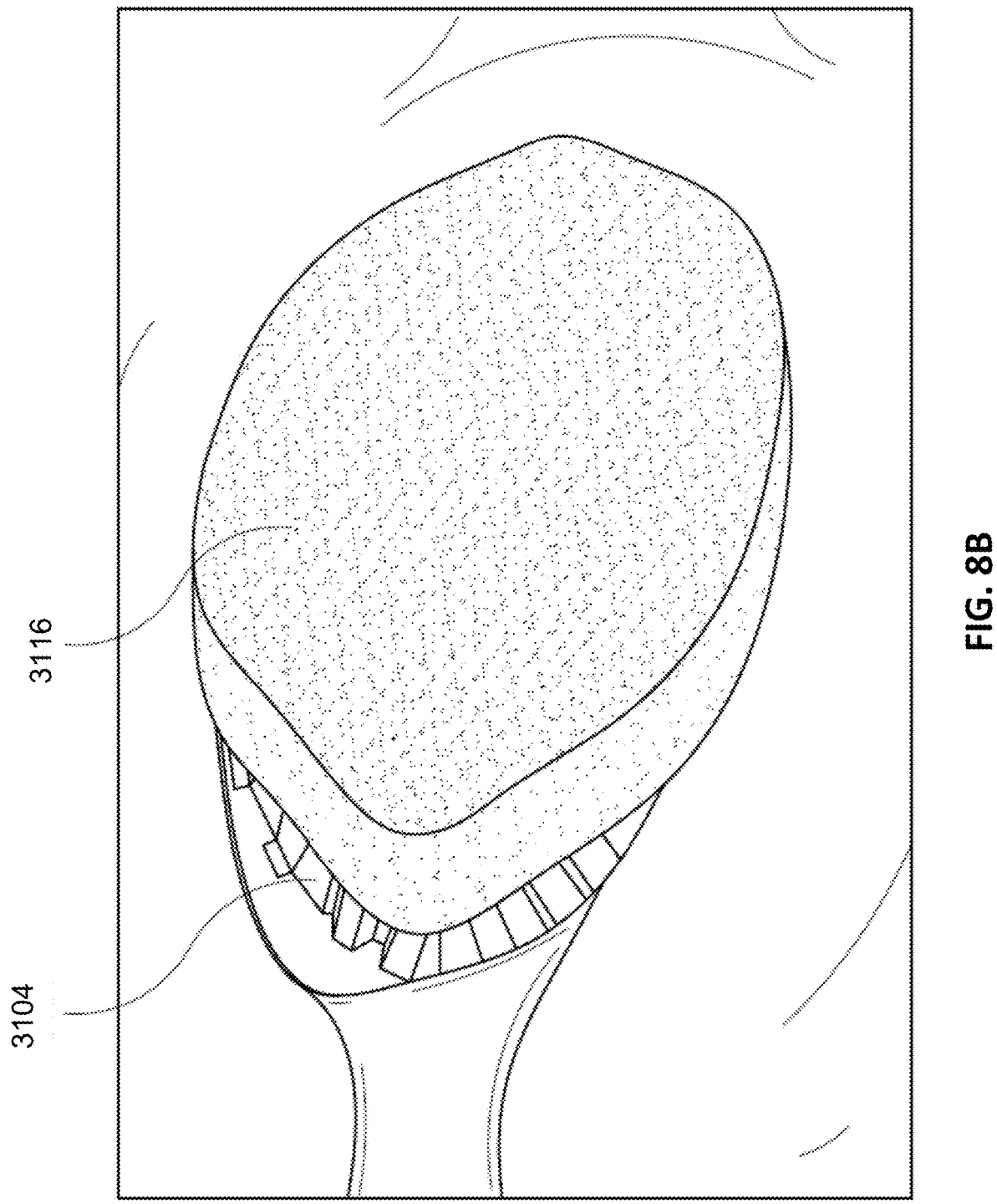
Figure 8C:
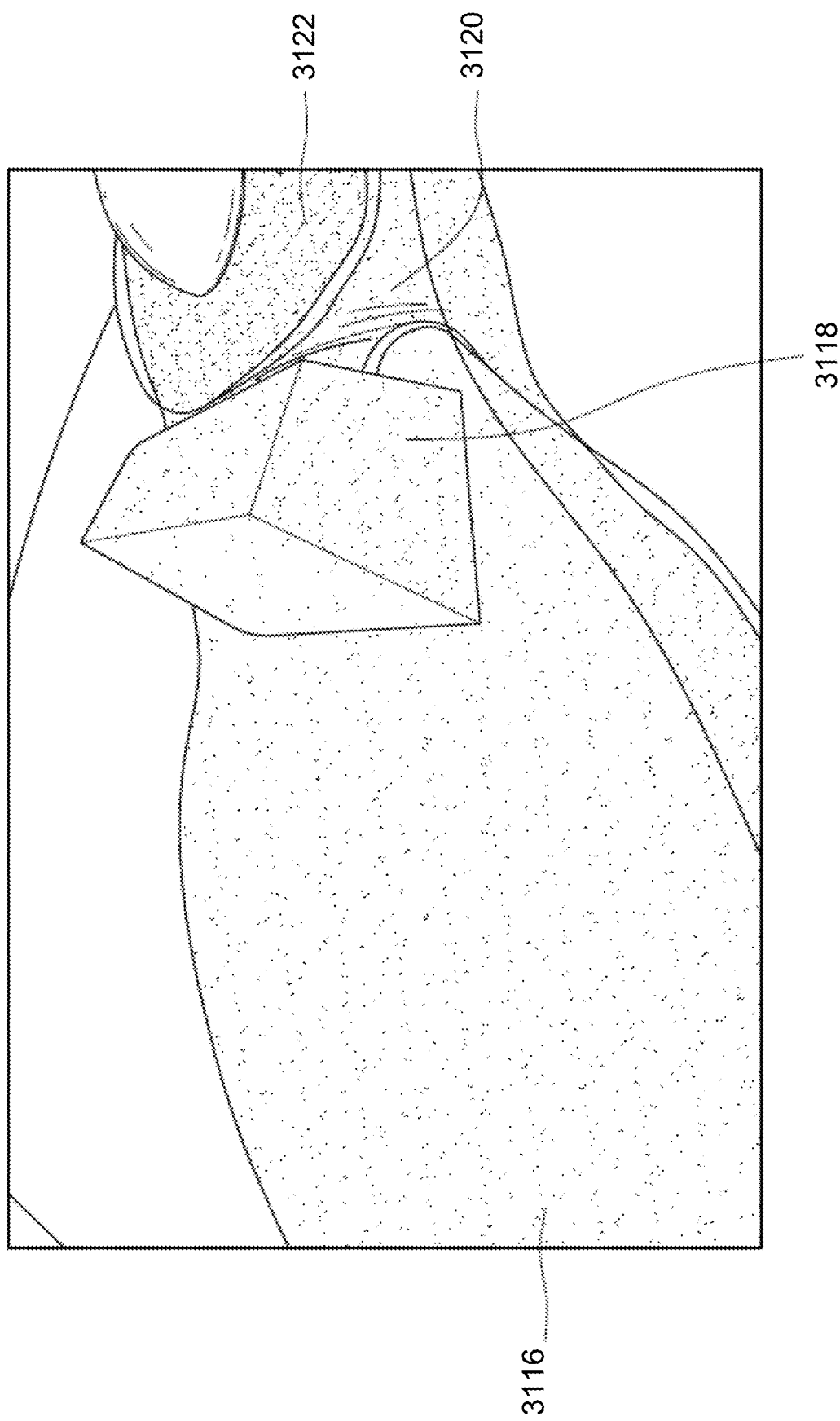

FIGS. 7A-B are photographs of a foam layer 3102 (for example, a 15 mm layer of foam), after shaping, placed into a wound bed 3100. In FIGS. 8A-C, a stabilizing structure 3104 similar to the stabilizing structures disclosed in FIGS. 2-3 or any other stabilizing structure described elsewhere in the specification, is in the shape of the wound. The stabilizing structure may be shaped into the shape of the wound via cutting or other suitable means or the stabilizing structure may initially be of a size that is readily accommodated by the wound. As displayed in FIG. 8B, the stabilizing structure 3104 may be placed into the wound. To assist with the insertion of the device into the wound bed, the device can be deformed slightly inwardly or horizontally to facilitate entrance into the wound site. In some embodiments, the device may be squeezed slightly during insertion and then release upon contact with the walls of the wound. In certain embodiments, the wound closure device 3104 may be placed such that the longitudinal sides of the matrix align with the longitudinal axis of the wound 3100. Continuing with FIG. 8B, another foam layer 3116 (for example, a 10 mm layer of foam) is placed on top of the wound closure device 3104.

FIG. 8C is a photograph of application of a port 3122 to the stabilizing structure and foam of FIGS. 8A-B. A bridging portion of foam 3118 may be placed in intimate contact with the foam layer 3116 at the edge of the wound. The bridging portion of foam 3118 may extend over intact skin, with a piece of drape 3120 placed between it and the intact skin. Further, a suction port 3122 may be connected to the bridging portion 3118 with a section of drape 3120 between. In alternative embodiments, the bridging portion 3118 and suction port 3122 may be placed on the wound during a different step depicted in FIGS. 7A-8B.

Figure 9:
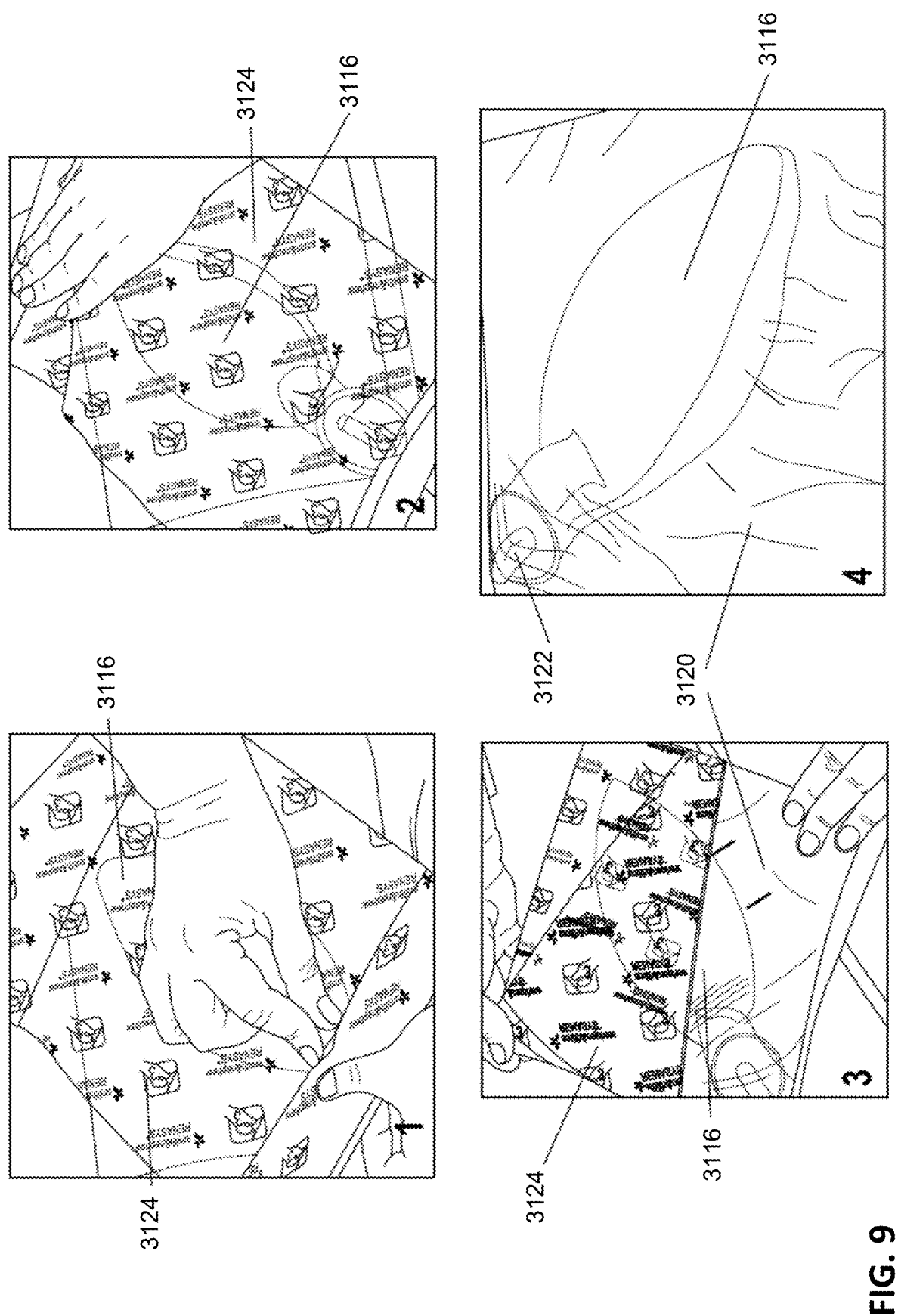
FIG. 9 contains photographs of embodiments of steps of a method of treating a wound.

In FIG. 9, as shown by steps 1-4, the device may be covered by one or more drapes 3120. A hole may be made in the drape covering the bridging portion of foam, and a suction port 3122 may be placed over the hole. A protective layer 3124 on the top surface of the one or more drapes may be removed after the drapes 3120 are applied. Once the drapes 3120 are applied and the port is in place, negative pressure may be applied to the wound through the drape from a vacuum source. The negative pressure can cause the stabilizing structure to collapse horizontally as described elsewhere in this specification. Tissue anchors which are adhered to the stabilizing structure through the porous layer may engage tissue of the wound and may facilitate closure of the wound.

In certain embodiments, the suction port may be placed directly over the central portion of the foam layer 3116. In such embodiments, the foam layer may collapse inward along with the stabilizing structure while under negative pressure, thereby collapsing the suction port. To avoid collapse, the suction port may be rigid in comparison to the foam and resist collapse. A washer may be placed inside, below, or around the suction port to provide rigidity and resist collapse.

In some embodiments, the suction port may be pre-attached to the top foam layer so that drapes can be positioned around the port. A hard port or a soft port may be used, such ports may further be used in combination with a washer such as described above. In further embodiments, the suction port could only partially collapse with the collapsing matrix while still maintaining the port opening for negative pressure.

Figure 10A:
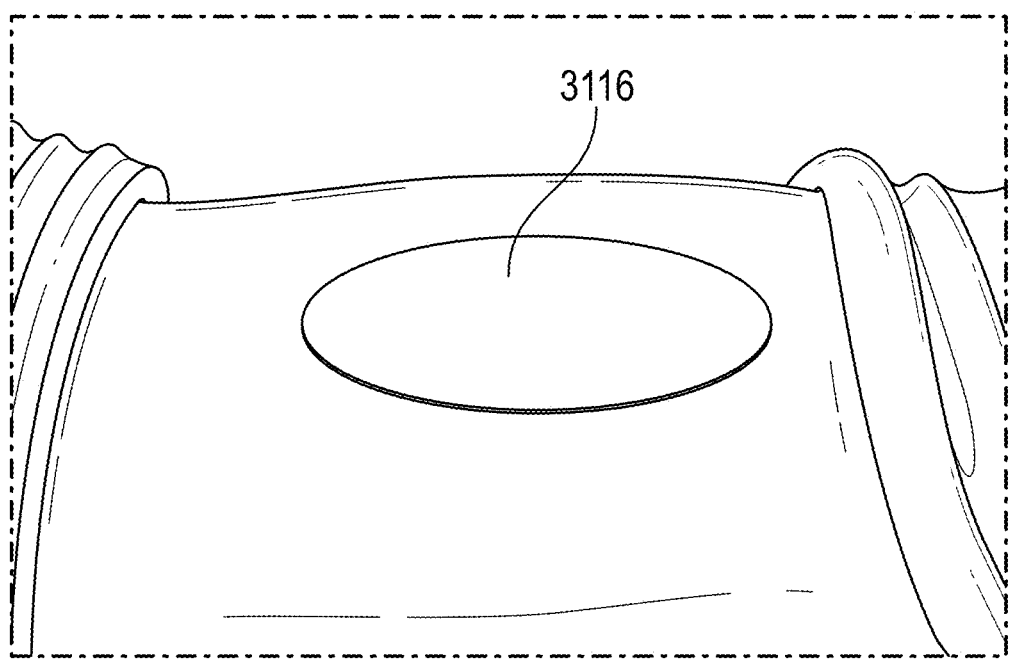
FIGS. 10A-G illustrate an embodiment of a method of treating a wound.
Figure 10B:
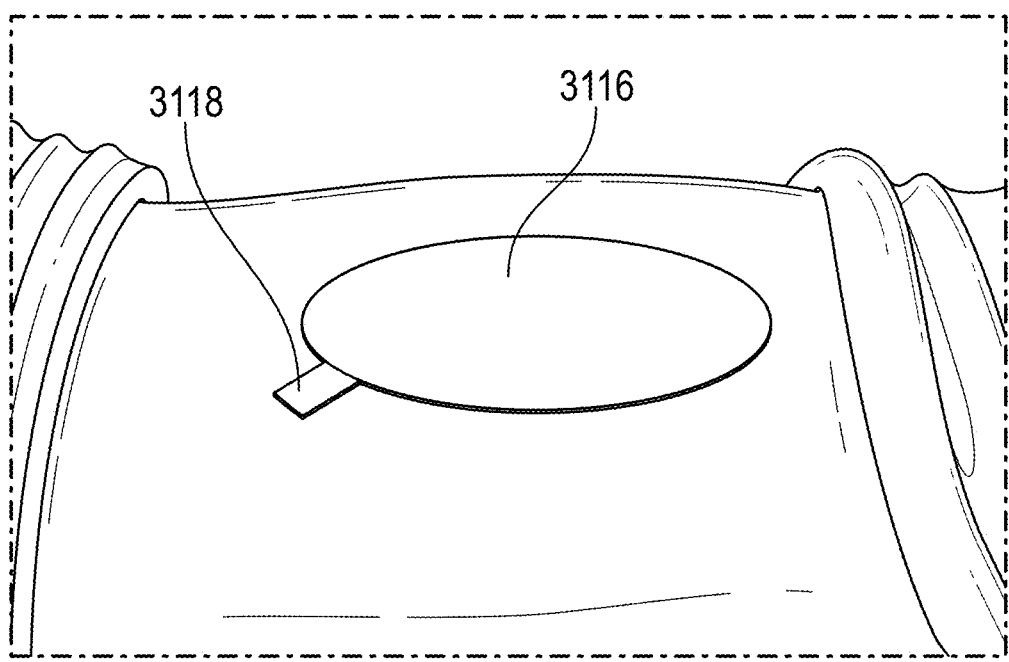
Figure 10C:
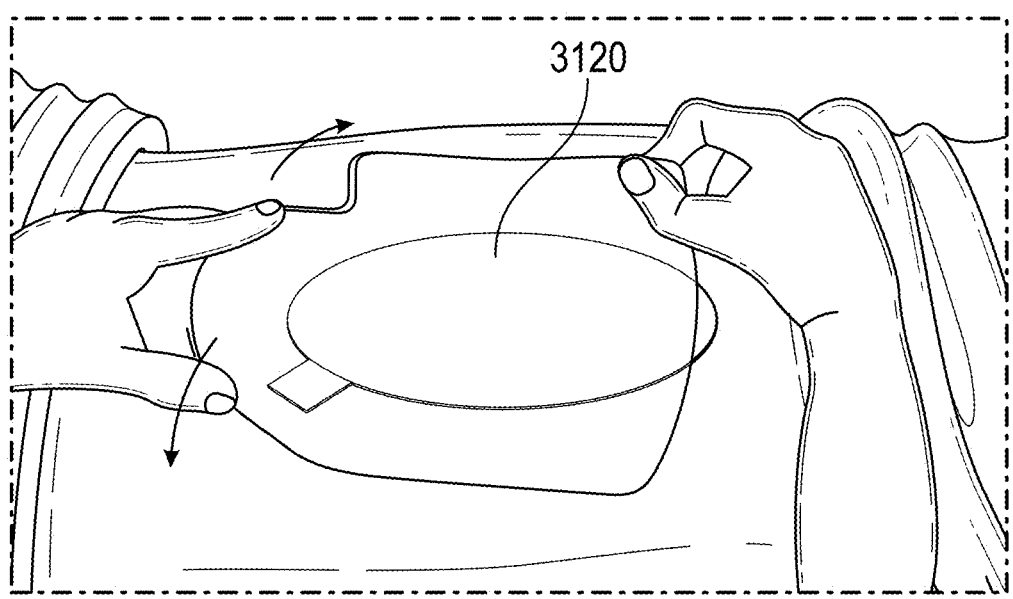
Figure 10D:
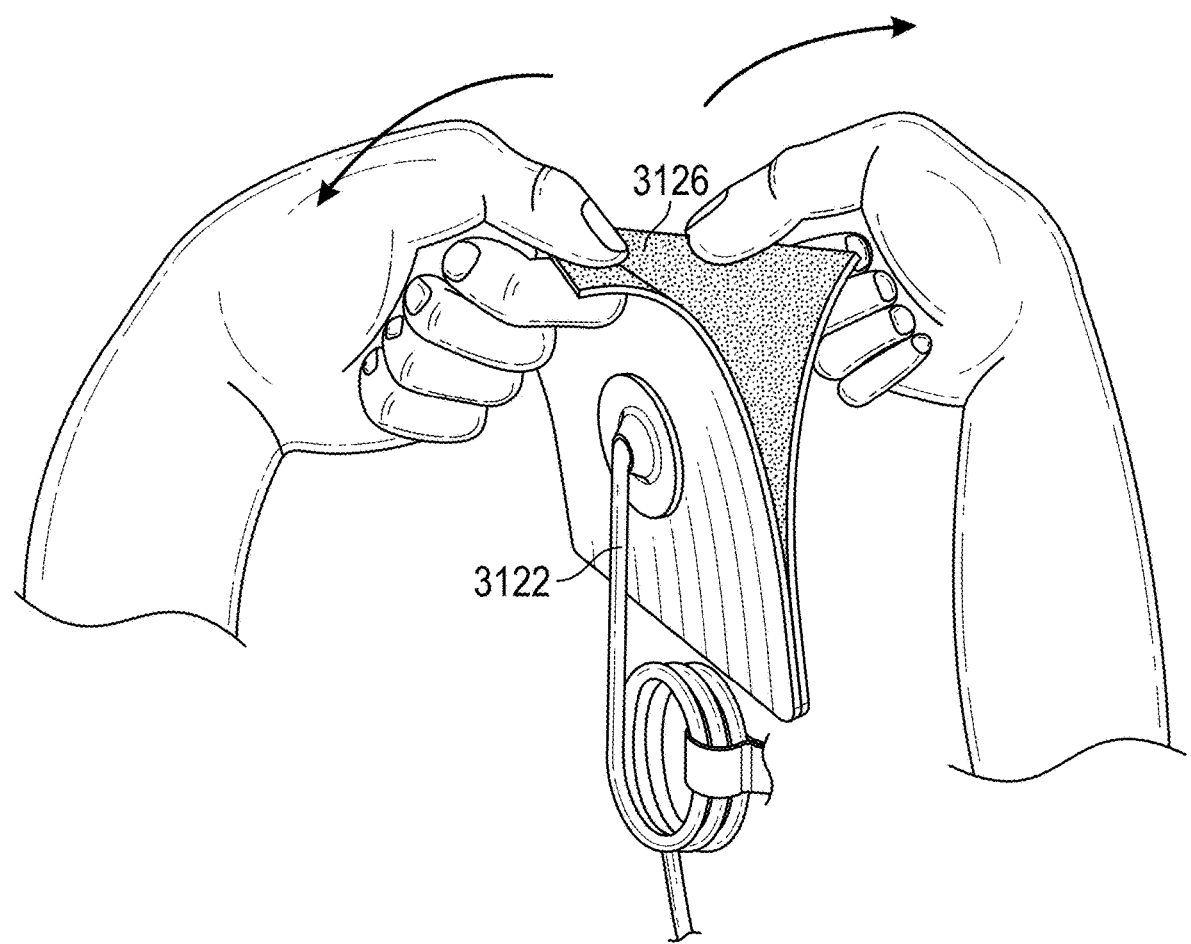
Figure 10E:
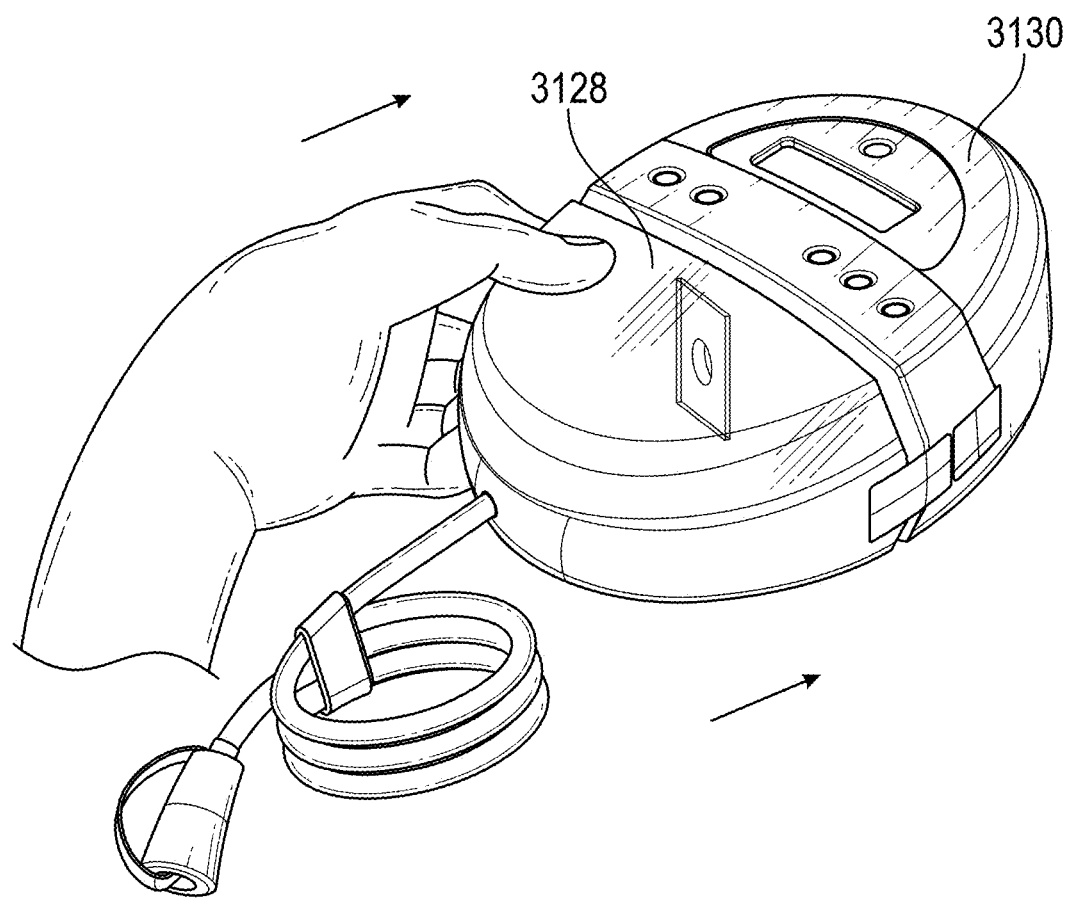
Figure 10F:
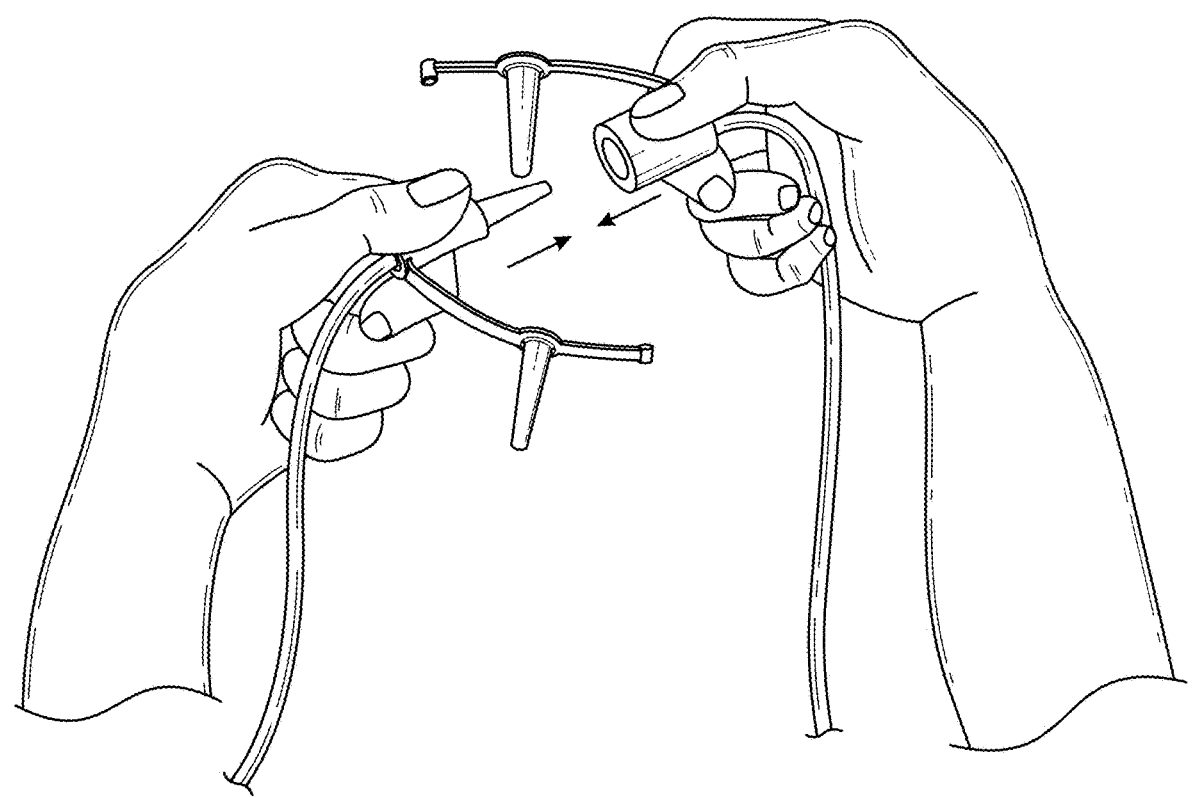
Figure 10G:
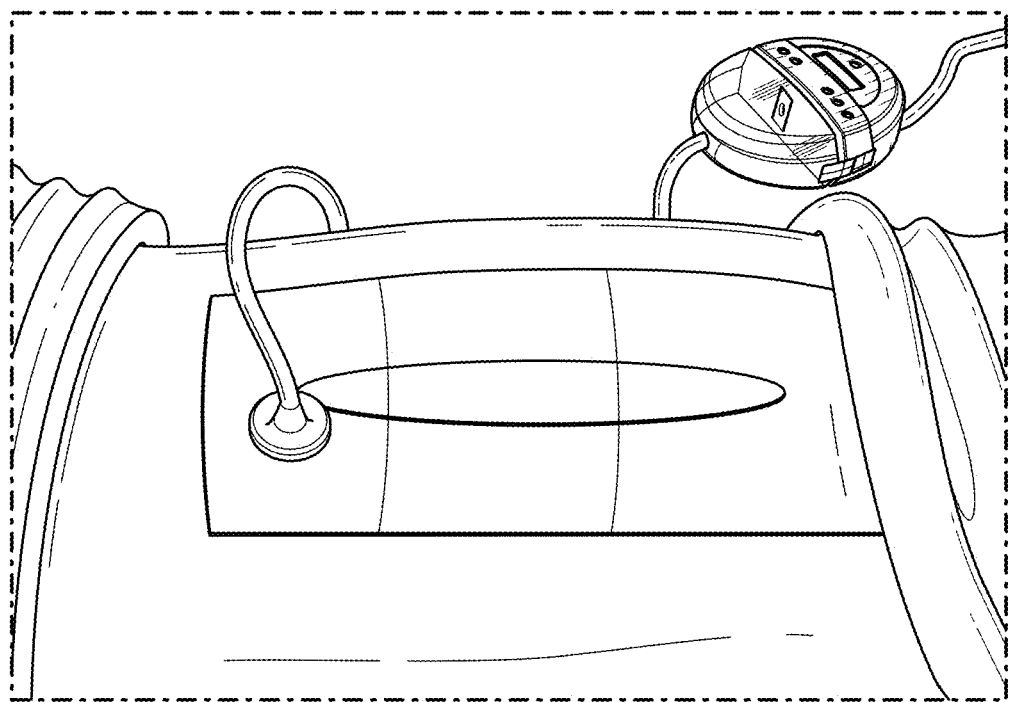

FIGS. 10A-C provide further illustrations of an upper foam layer 3116 being placed in a wound, followed by placing a bridging portion 3118 and placing one or more drapes or wound covers 3120. FIGS. 10D-10G illustrate an embodiment of several steps in a method for the treatment and closure of a wound. As illustrated in FIG. 10D, a suction port 3122 is separated from a release liner 3126 and later applied to a wound as depicted in FIGS. 7A-9. FIG. 10E illustrates a canister 3128 being inserted into a negative pressure wound therapy device 3130 in preparation for the collection of wound exudate. FIG. 10F illustrates the snap connection between the tubing connected to the suction port and the tubing connected to the negative pressure wound therapy device 3130. Once the connection has been made, negative pressure wound treatment may begin as depicted in FIG. 10G.

Further details regarding the wound closure devices, stabilizing structures, related apparatuses and methods of use that may be combined with or incorporated into any of the embodiments described herein are found elsewhere throughout this specification and in International Application No. PCT/US2013/050698, filed Jul. 16, 2013, published as WO 2014/014922 A1, the entirety of which is hereby incorporated by reference.

Figure 11A:
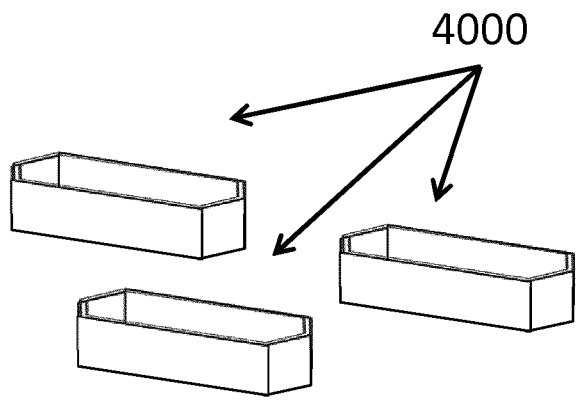
FIGS. 11A-C illustrate an embodiment of assembling a wound closure device.
Figure 11B:
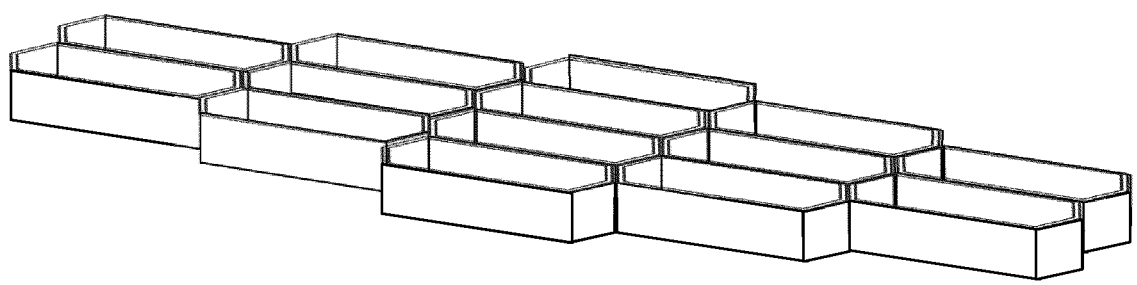
Figure 11C:
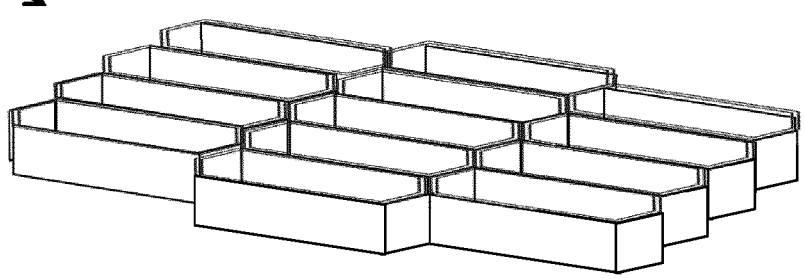
Figure 12:
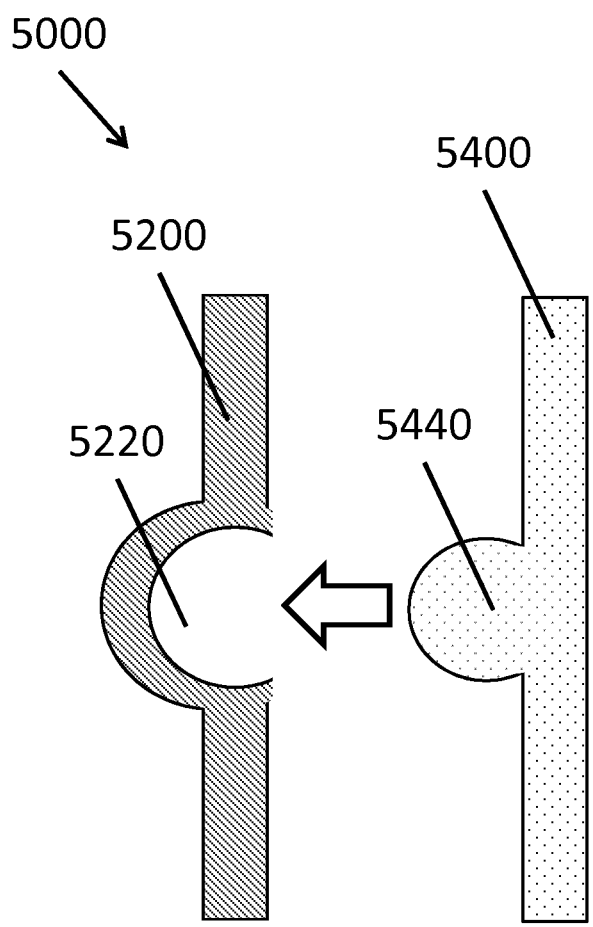
FIG. 12 illustrates an embodiment of a structure used to assemble a wound closure device.

Wound Closure Devices of FIGS. 11A-12

As discussed elsewhere in the specification, wound closure devices, stabilizing structures, and foam or porous materials may be shaped into the shape of a wound such that they can better accommodate the wound. Even if a stabilizing structure, foam or any porous material is not for insertion into a wound, it may be advantageously shaped into desirable size and shape to better serve its purpose. As discussed elsewhere in the specification, in some embodiments, wound closure devices, stabilizing structures, or foam or porous materials may be pre-shaped into any common shapes of wounds, such as an elliptical shape, and/or can be cut or tearable from a larger structure, such that the structure may be shaped into the shape of a wound. However, in some embodiments, any wound closure devices, stabilizing structures and/or foam/porous materials may be built from smaller building blocks, units or modules to form structures with desirable shapes. When structures or devices are built from smaller building blocks, they may be advantageously disassembled and/or reassembled to form another structures or devices with different shapes or sizes.

FIG. 11A illustrates an embodiment of building blocks 4000 that may be used to assemble stabilizing structures, foams or any other wound closure devices similar to those described in this specification. In some embodiments, the building blocks 4000 may be building blocks used to assemble for stabilizing structures having a size, shape and/or configuration similar to those illustrated in FIG. 2, 8A or 8B. As illustrated in FIG. 11A, one or more building blocks 4000 may have a hexagonal shape. In some embodiments, one or more building blocks 4000 may have a diamond shape, a square shape, a rhombus shape, any quadrilateral shape, any hexagonal shape, a triangular shape, or any other suitable shapes.

As illustrated in FIG. 11A, each of the building blocks 4000 may be defined by one or more walls and have a top end and a bottom end with an opening extending through the top and bottom ends, such that each of the building blocks 4000 become a cell when assembled to form a stabilizing structure. In some embodiments, the building blocks 4000 may be provided to have more than one cell for stabilizing structures, for example two, three, four, five or more cells, such that stabilizing structures can be built from building blocks having multiple cells.

Even though the illustrated building blocks 4000 are similar to cells of stabilizing structures described in this section or elsewhere in the specification, features and teachings described in relation to FIGS. 11A-C may be applicable to foam or porous materials/layers or any other components of wound closure devices described in this section or elsewhere in the specification. For example, in some embodiments, the building blocks 4000 may rather comprise a foam or porous material, such that it forms a larger foam or porous material structure or layer similar to those described in this section or elsewhere in the specification.

The building blocks 4000 may be constructed from any materials or methods described in relation to stabilizing structures or foam layer/structures, for example, flexible plastics such as silicone, polyurethane, rigid plastics such as polyvinyl chloride, semi-rigid plastics, semi-flexible plastics, biocompatible materials, composite materials, metals, and foam.

One or more building blocks may be adhered to one another via adhesive, Velcro®, or other suitable adhesive means. In some embodiments, magnets and/or suction cups may be used to keep the segments together. In some embodiments, one or more building blocks may have one or more attachment elements and/or one or more receiving elements. The attachment elements may be configured to serve to maintain attachment of a building block to another block until the attachment elements are separated from the receiving elements, for example by applying suitable force. Attachment elements may be prongs, hooks, tongues, screws, nails, or other suitable attachment means, and/or receiving elements may be in form of grooves, holes, windows, or any suitable means. For example, FIG. 12 illustrates an embodiment of part of building blocks 5200 and 5400 being reversibly attached to each other. The building block 5200 may have a receiving element 5220 while the building block 5400 may have an attachment element 5440 which is configured to fit into the receiving element 5220. In certain embodiments, each of building blocks may comprise both attachment elements and receiving elements. Building blocks may be assembled in a vertical direction, a horizontal direction, or both.

Turning back to FIGS. 11A-C, multiple building blocks 4000 may be adhered to one another side-by-side to provide a stabilizing structure or a foam or porous structure/layer, such as described in this section or elsewhere in the specification. FIGS. 11B-C illustrate such an embodiment of a stabilizing structure constructed from building blocks 4000. As shown in FIGS. 11B-C, by assembling building blocks 4000 in different ways, different structures may be provided. For example, the structure 4200 has approximately diamond shape, while the structure 4400 has approximately square shape. The structure 4200 may better fit to a wound having a length greater than a width, while structure 4400 may better fit to a wound having a width greater than a length. In some embodiments, one structure provided by assembling building blocks can be transformed to provide another structure with different size or shape by dissembling and reassembling building blocks. For example, a clinician may transform the structure 4200 into the structure 4400, or vice versa, by rearranging and/or adding/removing the building blocks 4000.

Wound Closure Devices of FIGS. 13A-14E

In some embodiments, stabilizing structures or foams may be provided as customizable building units having relatively simple shapes, (e.g., a single-row elongate structure, a square, a hexagon, etc.) which are customizable into different building units and/or assemble-able. Unlike building blocks described in relation to FIGS. 11A-C, customizable building units can be severed and customized into building units having different shape or size to be assembled to form stabilizing structures or foams. For example, each of customizable building units may have multiple reversibly-detachable cells or blocks, such that one can detach certain cells or blocks to transform the customizable building units into different building unit, and optionally assemble transformed unit structures to make a stabilizing structure or foam having desired size and/or shape. In some embodiments, customizable building units are provided in uniform size and shape, such that it can be produced or packaged more efficiently, while it can be easily customized.

Figure 13A:
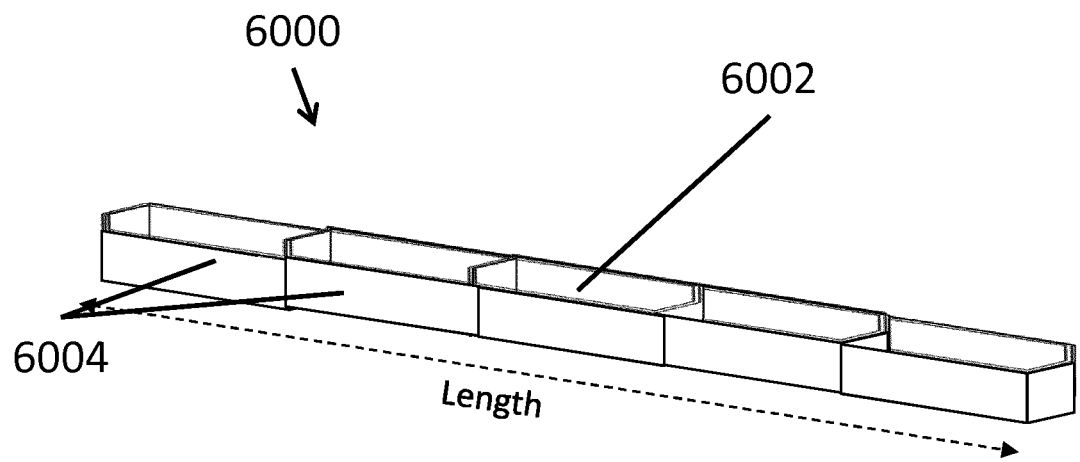
FIGS. 13A-C illustrate embodiments of units used to assemble a wound closure device and a method of providing them.
Figure 13B:
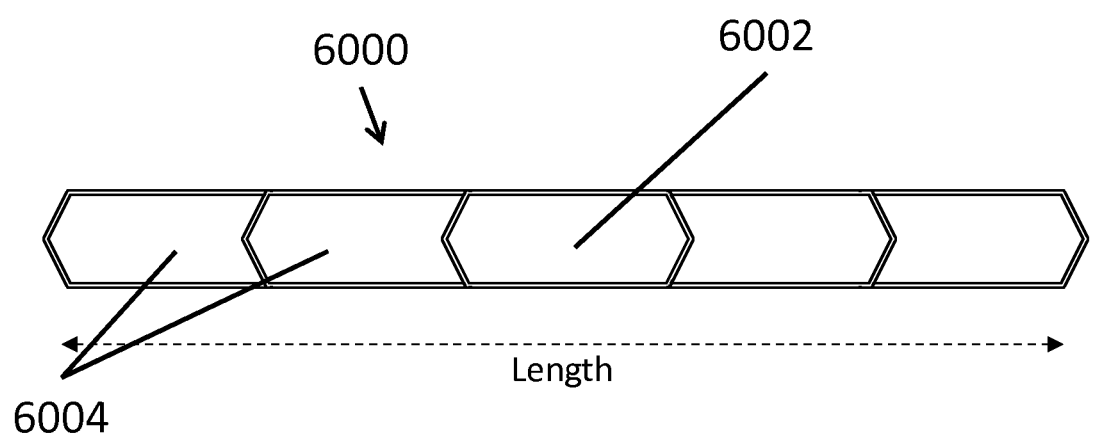

Stabilizing structures FIGS. 13A-B illustrates an embodiment of an elongate single-row customizable building unit 6000 including a central block or cell 6002 and a plurality of peripheral blocks or cells 6004 provided side-to-side in a single row. FIG. 13A-B illustrates a perspective view and a top view of the customizable building unit 6000, respectively. The illustrated embodiment of the customizable building unit 6000 may be similar with stabilizing structures described elsewhere in the specification, and blocks or cells 6002, 6004 may be similar with cells of the stabilizing structures, such that they are defined by one or more walls and each block or cell has a top end and a bottom end with an opening extending through the top and bottom ends. However, in some embodiments, the customizable building unit 6000 may be similar with foams or porous structures described elsewhere in the specification such that the top end and the bottom end do not have openings extending through the top and bottom ends. Even though the customizable building unit 6000 is illustrated to be similar with stabilizing structures described in this section or elsewhere in the specification, features and teachings described in relation to FIGS. 13A-F may be applicable to customizable building units similar to foam or porous materials or any other components of wound closure devices described in this section or elsewhere in the specification.

As illustrated in FIGS. 13A-B, the central cell 6002 and peripheral cells 6004 may have hexagonal shapes. In some embodiments, cells may have a diamond shape, a square shape, a rhombus shape, any quadrilateral shape, any hexagonal shape, a triangular shape, or any other suitable shapes. In some embodiments, the central cell 6002 and peripheral cells 6004 may have different shapes, such as shown in FIGS. 13A-B. In some embodiments, the central cell 6002 and peripheral cells 6004 may have a uniform shape. In some embodiments, peripheral cells 6004 may have same shape and sizes such that they are interchangeable. In some embodiment, peripheral cells 6004 may have two or more different shapes or sizes.

The customizable building unit 6000 may comprise precuts defining cells 6002 and 6004, such that each cell can be easily disassembled, cut out or torn to reduce its length. In some embodiments, the unit 6000 may be constructed by assembling each of cells 6002 and 6004. Cells 6002 and 6004 may be attached with adhesives, Velcro®, other mechanical means, or any other suitable means such as described in more details below. Cells 6002 and 6004 may be reversibly detachable such that cells 6002 and 6004 may be disassembled without substantially damaging any part of cells, for example by application of force.

Figure 13C:
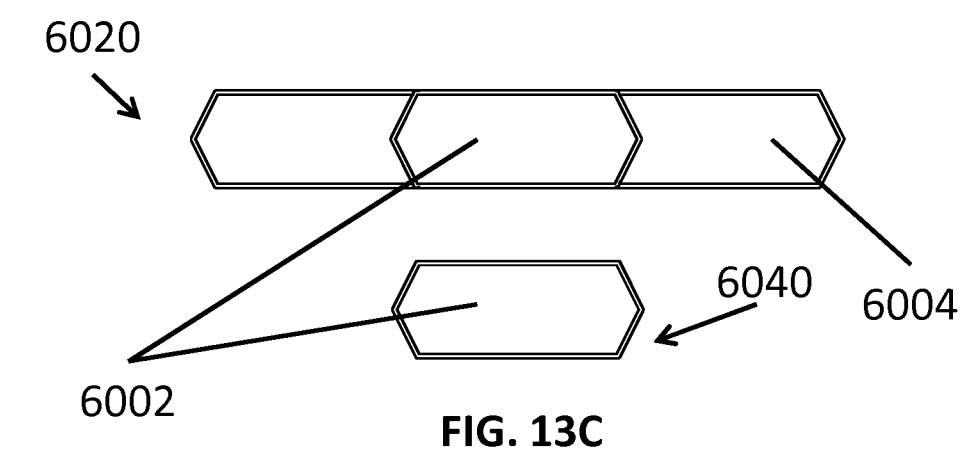

In some embodiments, the length of single-row building units such as the customizable unit 6000 may be adjusted by adding/removing peripheral cells 6002. FIG. 13C illustrates single-row building units 6020 and 6040 similar to the unit 6000, but having fewer numbers of blocks or cells. The building units 6020 and/or 6040 may be prepared by removing peripheral cells 6004 from the customizable building unit 6000 of FIGS. 13A-B. In some embodiments, shorter units may be prepared by removing one, two, three, four, five, or more peripheral cells 6004 from a longer unit. Alternatively, the building units 6020 and 6040 may be constructed by assembling cells 6002 and 6004. The shortest unit 6040 may be the central cell 6002.

Figure 13D:
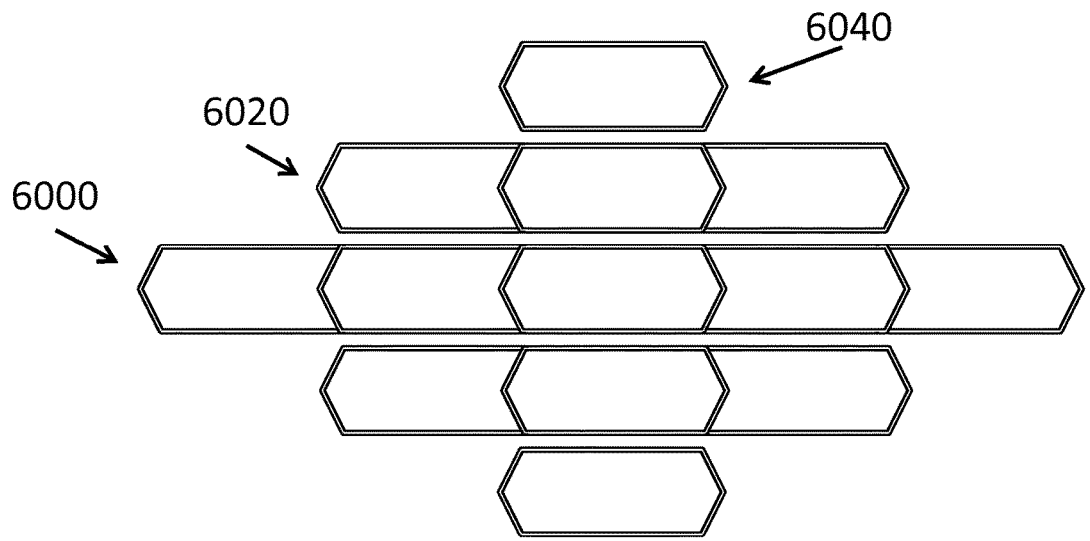
FIGS. 13D-E illustrate an embodiment of a method of assembling a wound closure device.
Figure 13E:
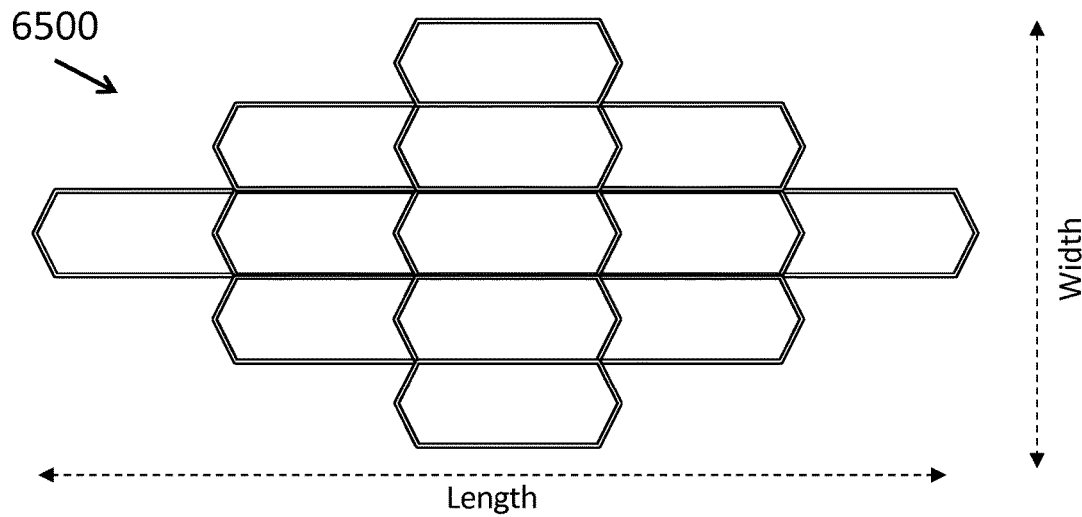
Figure 13F:
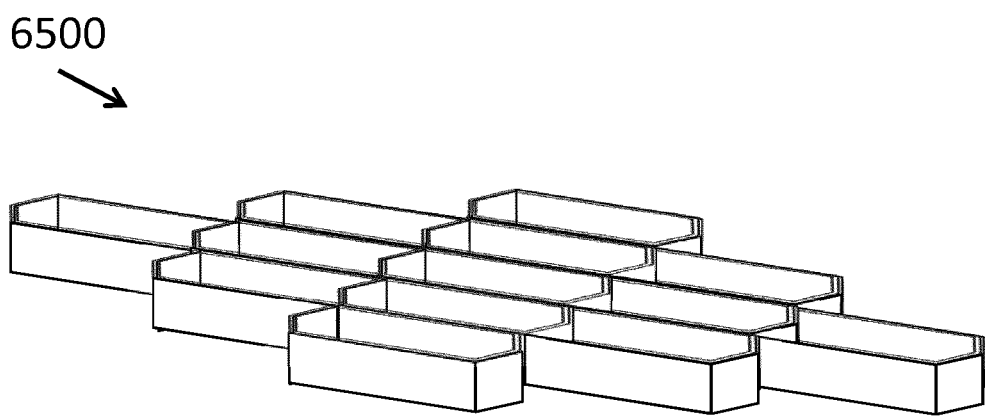
FIG. 13F illustrates an embodiment of a wound closure device provided by the method illustrated by FIGS. 13D-E.

The building units 6020 and 6040 provided by adjusting the customizable building unit 6000 may be assembled to provide a more complex structure. FIG. 13D illustrates an embodiment of a collection of single-row building units 6000, 6020, and 6040 having different lengths, arranged in an approximately diamond shape before assembly. FIGS. 13E-F illustrate a multi-row structure 6500 formed by assembling the building unit 6000 and two of each of the building units 6020 and 6040 as arranged in FIG. 13D. By assembling multiple single-row units, one may increase the width of the structure. The illustrated multi-row structure 6500 has approximately a diamond shape. In some embodiments, the multi-row structure 6500 may have approximately an elliptical shape, a circular shape, or any other shapes. In some embodiments, the multi-row structure 6500 may be a stabilizing structure similar to stabilizing structures described in this section or elsewhere in the specification, such that it collapses by collapsing one or more cells.

In some embodiments, a clinician may decrease the size of the multi-row structure 6500 as the size of the wound decrease as the wound heals. In some embodiments, a kit may include multiple customizable single-row units, such that a clinician can freely attach and/or detach cells of single-row units, and freely attach and/or detach multiple single-row units to accommodate various size and shape of the wound. Interface between each cell and each single-row unit may comprise means to reversibly attach cells and structures, such as Velcro®, adhesives, anchors, hooks, prongs or any other suitable means, such as described in this section or elsewhere in the specification. In some embodiments, the single-row unit 6000 may be replaced with any other structures having cells or blocks.

Figure 14A:
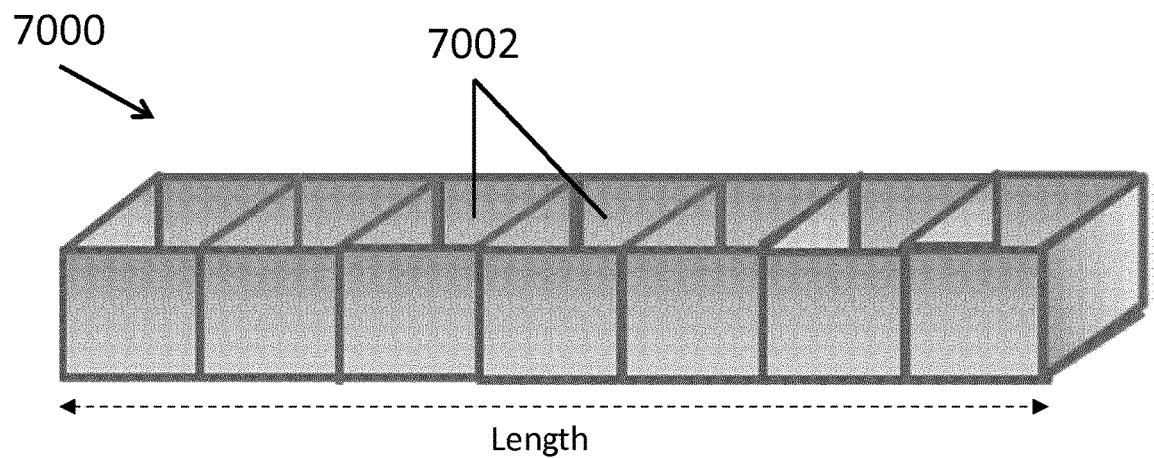
FIGS. 14A-D illustrate embodiments of units used to assemble a wound closure device and a method of providing them.
Figure 14B:
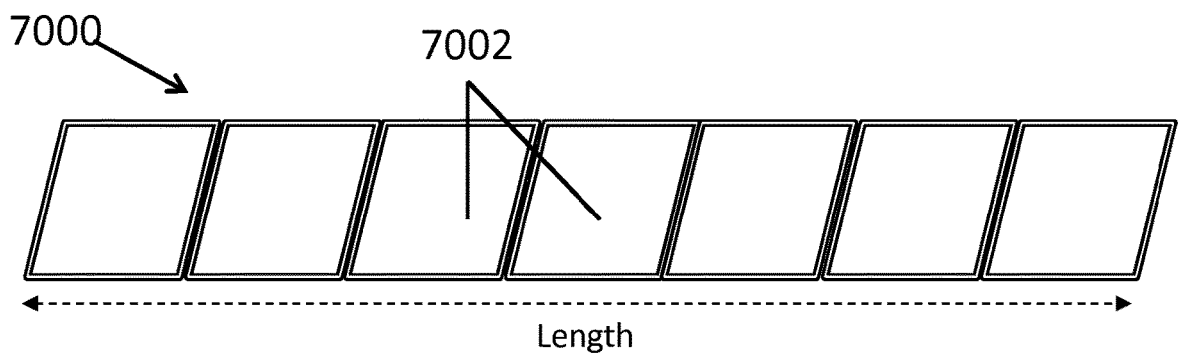

FIGS. 14A-B illustrate a customizable single-row building unit 7000 similar to the single-row building unit 6000 shown in FIGS. 13A-B. The building unit 7000 contains a plurality of cells or blocks 7002 provided side-by-side. One or more cells or blocks 7002 may have a same size and shape. In some embodiments, all cells or blocks 7002 have same shape and/or size. Each of cells or blocks 7002 may have a diamond shape such as shown in FIGS. 14A-B. In some embodiments, cells or blocks 7002 may have a hexagonal shape, a square shape or any other suitable shapes. The building unit 7000 may comprise precuts defining cells 7002.

Figure 14C:
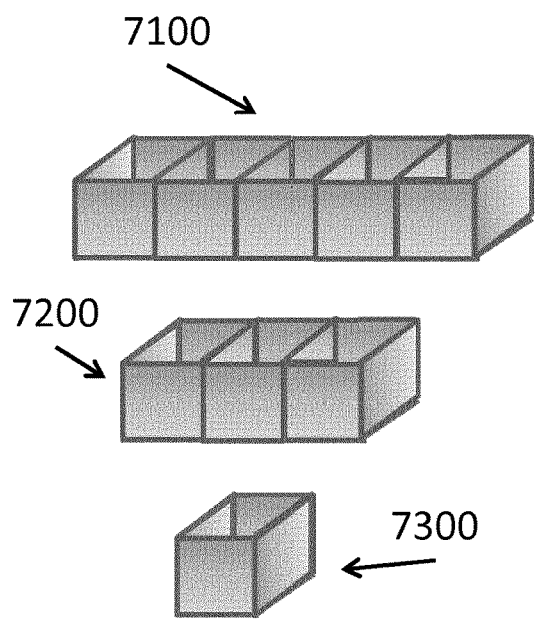
Figure 14D:
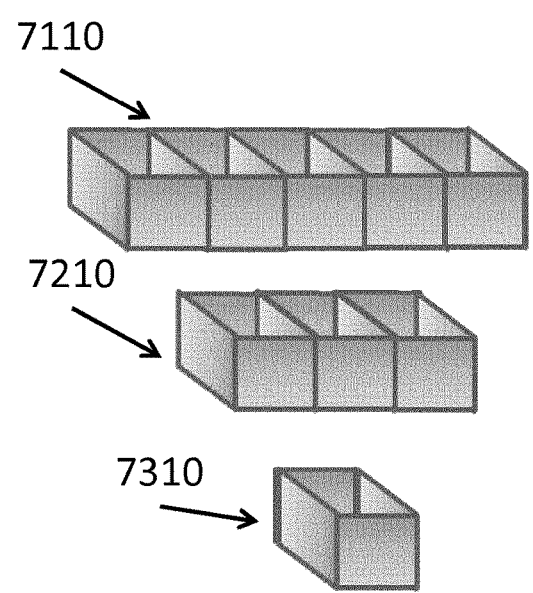

FIG. 14C illustrates single-row building units 7100, 7200, and 7300 which may be provided from the customizable unit 7000 by methods similar to those described in relation to FIGS. 13A-C, for example tearing along precuts defining cells 7002. FIG. 14D illustrates single-row building units 7110, 7210, and 7310 which mirrors the units 7100, 7200, and 7300 respectively. The units 7110, 7210, and 7310 may be provided by flipping the units 7100, 7200, and 7300 upside-down, respectively.

Figure 14E:
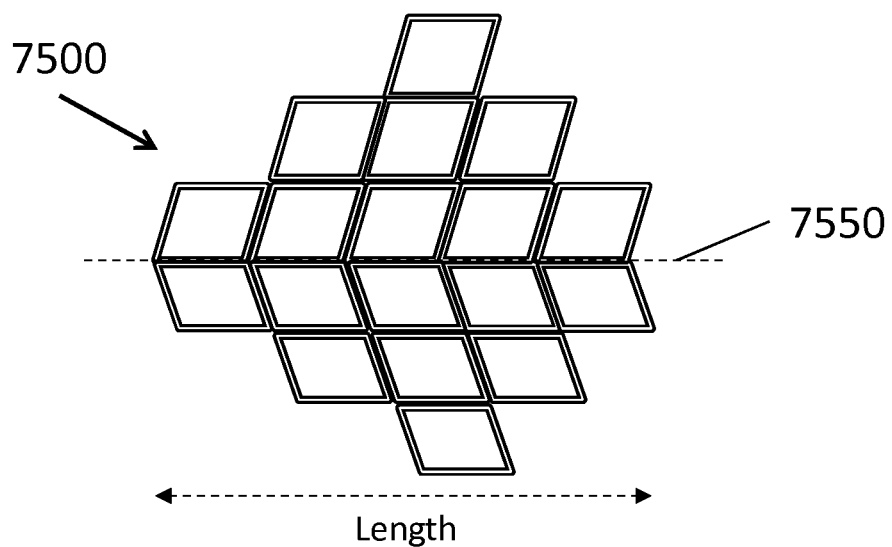
FIG. 14E illustrates an embodiment of a wound closure device provided by assembling units illustrated by FIGS. 14A-D.
Figure 14F:
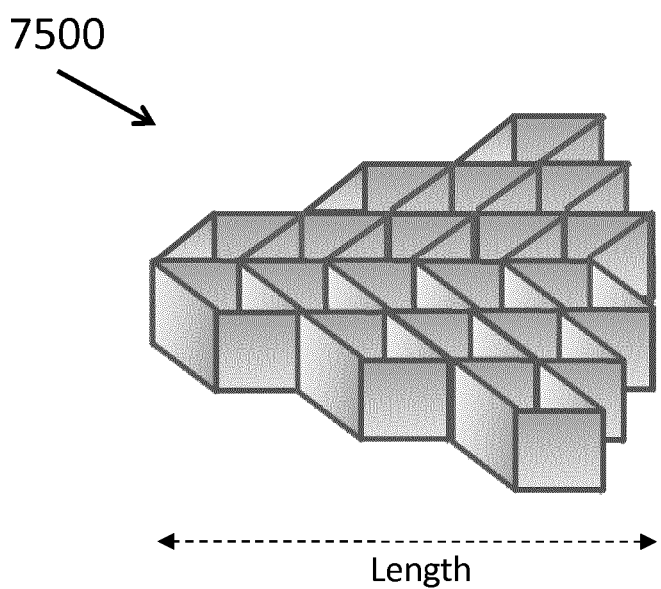
FIG. 14F illustrates a plan view of the wound closure device of FIG. 14E.
Figure 14G:
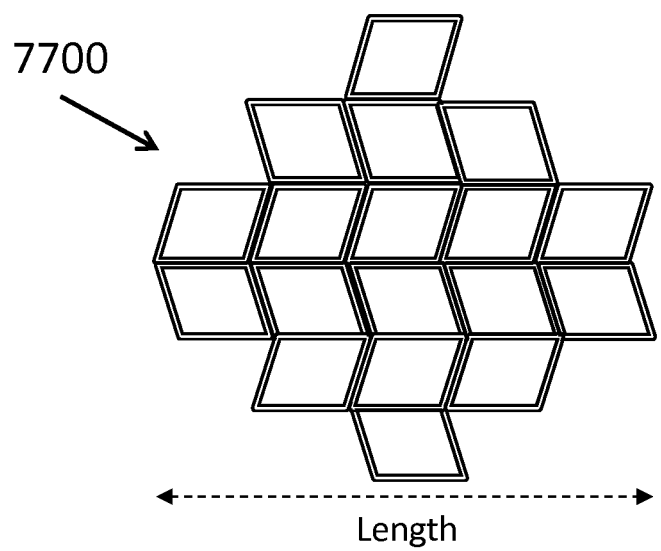
FIG. 14G illustrates another embodiment of a wound closure device provided by assembling units illustrated by FIGS. 14A-D.

FIGS. 14E-F illustrate an embodiment of a multi-row structure 7500, which may be provided by adhering the building units 7100, 7200, 7300, 7110, 7210, and 7310 by methods described in this section or elsewhere in the specification. FIG. 14E illustrates a plan view of the structure 7500 from the top. As shown in FIG. 14E, single-row units may be assembled to provide the structure 7500 such that cells may be angled in alternative directions, all in one direction on a side of a midline 7550, and all in another direction on the other side of the midline 7550. FIG. 14F is a perspective view of the structure 7500. FIG. 14G illustrates a plan view of an embodiment of a multi-row structure 7700, which also may be provided by adhering the building units 7100, 7200, 7300, 7110, 7320, and 7310 similarly to the structure 7500, but in a different configuration. As shown in FIG. 14G, single-row units may be assembled to provide the structure 7700 such that cells may be angled in alternative directions, all in one direction on a row, and all in another direction on the adjacent row(s).

Figure 15A:
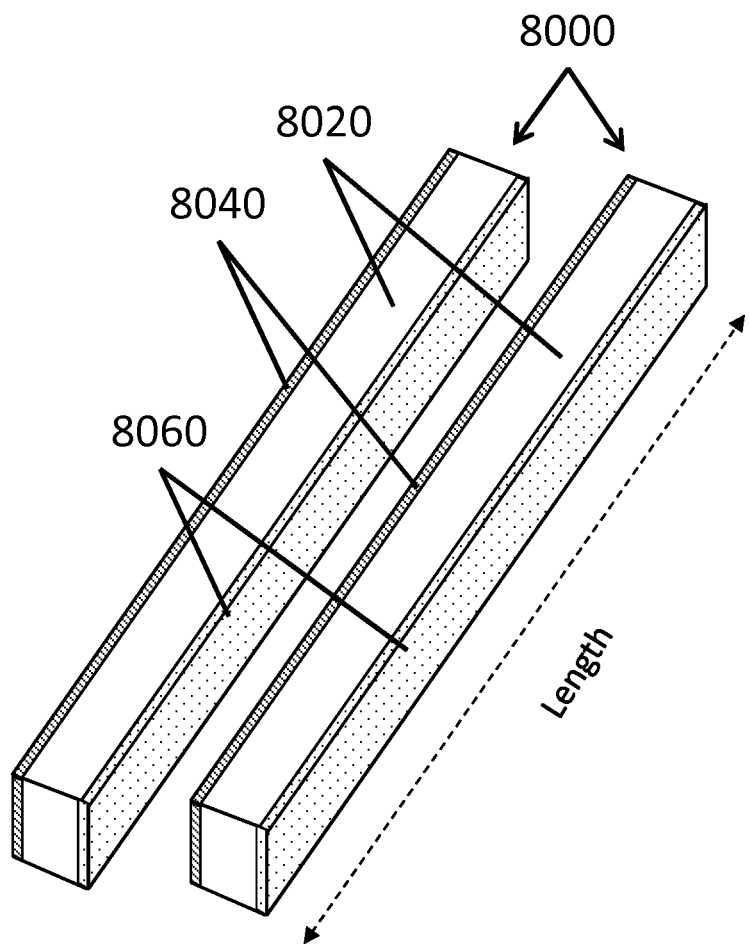
FIG. 15A illustrates an embodiment of units used to assemble a wound closure device.
Figure 15B:
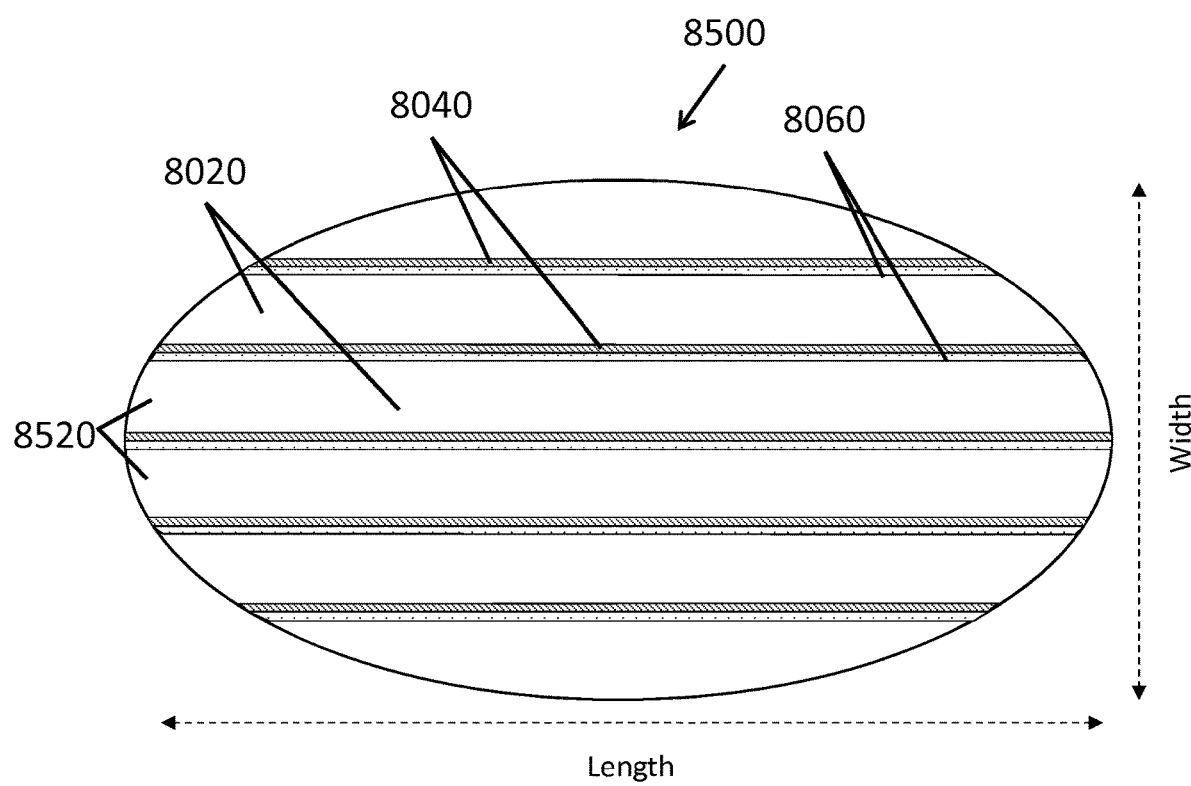
FIG. 15B illustrates an embodiment of a wound closure device provided by assembling units illustrated in FIG. 15A and/or modifications thereof.

Wound Closure Devices of FIGS. 15A-B

As described in relation to FIGS. 13A-14E, stabilizing structures or foam structure/layers may be constructed from customizable building units comprising detachable blocks or cells. Even though FIGS. 13A-14E illustrates cells or blocks similar to cells of stabilizing structures, features described in relation to FIGS. 11A-14E may be applied to foam or porous structures or layers. In some embodiments, customizable building units for foam structure/layer may not have cell-like features, for example because foam structure or layer does not need to have cells, and customizable building units may be customized by freely tearing or cutting parts along the units.

FIG. 15A illustrates such an embodiment of elongate customizable building units 8000. Each of the building units 8000 may contain foam or porous material 8020, and attachment sections 8040 and 8060. The building units 8000 may be adhered to one another by attaching the section 8040 of one unit to the section 8060 of another unit. Sections 8040 and sections 8060 may be configured to be reversibly attached to each other by any means described in this section or elsewhere in the specification, for example, by Velcro®, adhesives, anchors, hooks, prongs or any other suitable means. The length and shape of each of the building units 8000 may be adjusted by tearing or cutting. In some embodiments, each of the building units 8000 may comprise precuts such that each of the building units 8000 may be torn along precuts.

FIG. 15B illustrates a foam structure 8500 built from multiple units which are adjusted from the customizable building units 8000 to have different lengths, and adhered to one another side-by-side. The foam structure 8500 may have an at least partially elliptical shape. In some embodiments, the structure 8500 may have at least approximately diamond shape, a square shape, a rectangular shape, or any other suitable shapes to better accommodate to a wound. In some embodiment, the size of the foam structure may be adjusted by removing and/or adding building units. For example, the width of the structure 8500 may be reduced by removing units 8520 and re-assembling the rest of the structure 8500.

Other Variations

Although this disclosure describes certain embodiments, it will be understood by those skilled in the art that many aspects of the methods and devices shown and described in the present disclosure may be differently combined and/or modified to form still further embodiments or acceptable examples. All such modifications and variations are intended to be included herein within the scope of this disclosure. Indeed, a wide variety of designs and approaches are possible and are within the scope of this disclosure. No feature, structure, or step disclosed herein is essential or indispensable. Moreover, while illustrative embodiments have been described herein, the scope of any and all embodiments having equivalent elements, modifications, omissions, combinations (e.g., of aspects across various embodiments), substitutions, adaptations and/or alterations as would be appreciated by those in the art based on the present disclosure. While certain embodiments have been described, these embodiments have been presented by way of example only, and are not intended to limit the scope of protection.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially"

as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A wound closure device comprising:
   a plurality of building blocks and/or building units configured to be adhered to or attached to each other to form an assembled structure for insertion into or placement over a wound, the assembled structure configured to collapse significantly more in a first plane than in a second plane upon application of negative pressure;
   wherein each building block and/or building unit comprises a cell defined by two or more walls, the cell comprising an attachment element positioned on a wall of the cell, the cell reversibly securable to the assembled structure such that the cell is configured to be removed from the assembled structure and re-secured to the assembled structure by the attachment element; and
   wherein the cell comprises a top end and a bottom end with an opening extending through the top and bottom ends, the opening spanning a width of the cell from a wall to an opposing wall.

2. The wound closure device of claim 1, wherein the building blocks and/or building units are configured to form an assembled stabilizing structure comprising a plurality of cells defined by two or more walls, wherein in the assembled stabilizing structure cells are provided side-by-side in a horizontal plane.

3. The wound closure device of claim 1, wherein one or more of the building blocks and/or building units comprises receiving elements configured to receive the attachment elements of one or more of the building blocks and/or building units.

4. The wound closure device of claim 1, wherein one or more of the building blocks and/or building units has an elongate shape with a uniform width.

5. The wound closure device of claim 1, wherein each of the building blocks and/or building units comprises one or more cells provided in a single row.

6. The wound closure device of claim 1, wherein each of the building blocks and/or building units comprises cells having a uniform shape and size.

7. The wound closure device of claim 1, wherein each of the building blocks and/or building units consists of one cell.

8. The wound closure device of claim 1, wherein each of the building blocks and/or building units comprises at least one cell having a triangular, quadrilateral or hexagonal shape.

9. The wound closure device of claim 1, wherein each of the building blocks and/or building units comprises foam or porous material.

10. The wound closure device of claim 9, wherein one or more building blocks and/or building units further comprises precuts defining frangible portions of the foam or porous material.

11. The wound closure device of claim 1, wherein one or more of the plurality of building blocks and/or building units is configured to be cut or torn.

12. The wound closure device of claim 1, further comprising a source of negative pressure.

13. The wound closure device of claim 1, further comprising a drape placed over the wound.

14. The wound closure device of claim 13, further comprising a port, wherein the port is configured to transmit negative pressure through the drape.

15. The wound closure device of claim 1, further comprising an organ protection layer.

16. A method of treating a wound, comprising:
    adhering a plurality of building blocks and/or building units to one another to provide a stabilizing structure;
    inserting the stabilizing structure into the wound;
    wherein the plurality of building blocks and/or building units comprise one or more cells defined by two or more walls, each cell reversibly securable to the stabilizing structure such that the cell is configured to be removed from the stabilizing structure and re-secured to the stabilizing structure, individual cells comprising a top end and a bottom end with an opening extending through the top and bottom ends, the opening spanning a width of the individual cell from one wall to an opposing wall; and
    wherein the plurality of building blocks and/or building units are configured to be adhered to one another to provide the stabilizing structure, the stabilizing structure configured to collapse significantly more in a first plane than in a second plane upon application of negative pressure.

17. The method of claim 16, further comprising adjusting the size and/or shape of the building blocks and/or the building units by detaching one or more cells from the building blocks and/or the building units, wherein one or more blocks and/or units have two or more cells.

18. The wound closure device of claim 1, wherein the plurality of building blocks and/or building units are separate from one another.

* * * * *